United States Patent [19]

Verheyden et al.

[11] Patent Number: 5,449,664

[45] Date of Patent: Sep. 12, 1995

[54] ANTIVIRAL AGENTS

[75] Inventors: Julien P. H. Verheyden, Los Altos; Hans Maag, Menlo Park; Ernest J. Prisbe, Los Altos, all of Calif.

[73] Assignee: Syntex (U.S.A.) Inc., Palo Alto, Calif.

[21] Appl. No.: 808,968

[22] Filed: Dec. 16, 1991

Related U.S. Application Data

[63] Continuation of Ser. No. 524,773, May 17, 1990, abandoned, which is a continuation-in-part of Ser. No. 274,538, Nov. 21, 1988, abandoned.

[51] Int. Cl.⁶ .................... A61K 31/70; C07H 19/00
[52] U.S. Cl. ........................ 514/45; 514/46; 514/47; 514/48; 514/49; 514/50; 514/51; 514/934; 536/26.12; 536/26.13; 536/26.7; 536/26.72; 536/26.8; 536/27.14; 536/27.6; 536/27.81; 536/28.5; 536/28.53
[58] Field of Search ............... 536/27, 28, 29, 26.12, 536/26.13, 26.7, 26.72, 26.8, 27.14, 27.6, 27.81, 28.5, 28.53; 514/45, 46, 47, 48, 49, 50, 51, 934, 885

[56] References Cited

U.S. PATENT DOCUMENTS

| | | | |
|---|---|---|---|
| 3,817,982 | 6/1974 | Verheyden et al. | 536/24 |
| 3,910,885 | 8/1975 | Moffatt et al. | 536/24 |
| 3,928,319 | 12/1975 | Jenkins et al. | 536/27 |
| 4,145,531 | 3/1979 | Eckstein et al. | 536/27 |
| 5,192,749 | 3/1993 | O-Yang et al. | 514/45 |

OTHER PUBLICATIONS

Verheyden et al., Ann. N.Y. Acad. Sci. vol. 255, pp. 151–165 (1975).
"Strategies for antiviral therapy in AIDS", Hiroki Mitsuya and Samual Broder, Nature, 325, 26 Feb. 1987.
"AIDS: Modern Concepts and Therapeutic Challenges; Chapter 18, Rapid in Vitro Systems for Assessing Activity of Agents Against HTLV-III/LAV", Samual Broder, Ed., Marcel-Dekker, N.Y. 1987, pp. 303–333.
"Inhibition of HIV–Induced Cytopathogenicity in vitro by 3′-Azido-2′,3′-Dideoxyguanosine", Heinz Hartmann, Gerhard Hunsmann and Fritz Eckstein, The Lancet, Jan. 3, 1987.
"Selective Inhibition of Human Immunodeficiency Virus (HIV) by 3′-Azido-2′-3′-Dideoxyguanosine in vitro", Masanori Baba, Rudi Pauwels, Jan Balzarini, Piet Herdewijn and Erik de Clercq, Biochemical and Biophysical Research Communications, pp. 1080–1086, Jun. 30, 1987.

Primary Examiner—Douglas W. Robinson
Assistant Examiner—James O. Wilson
Attorney, Agent, or Firm—Susan J. Friedman; Theodore J. Leitereg; Alan M. Krubiner

[57] ABSTRACT

Nucleoside compounds of the formula

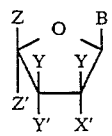

wherein:

B is a purine or a pyrimidine;

X and X′ are H, OH or F, provided that at least one is H;

Y and Y′ are H, OH, OCH₃ or F, provided that at least one is H;

Y′ and Z together form a cyclic phosphate ester, provided that Y is H; or

Z is

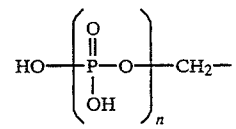

where n is zero, one, two or three; and Z′ is N₃ or OCH₃;

provided that when X′ and Y′ are OH and Z′ is N₃, B is not cytosine, and when X′ and Y′ are OH and Z′ is OCH₃, B is not uracil, adenine or cytosine;

and the pharmaceutically acceptable esters, ethers and salts thereof, have been found to have potent antiviral activity with a high therapeutic ratio.

21 Claims, No Drawings

ANTIVIRAL AGENTS

CROSS-REFERENCE TO RELATED APPLICATIONS

This is a continuation of application Ser. No. 07/524,733, filed May 17, 1990, now abandoned, which is a continuation-in-part of U.S. application Ser. No. 07/274,538, filed Nov. 21, 1988, now abandoned, which is incorporated herein by reference.

This application also claims priority from European Patent Application No. 89121451.2, filed Nov. 20, 1989, incorporated herein by reference and itself claiming priority from said application Ser. No. 274,538.

BACKGROUND OF THE INVENTION

1. Field of the Invention

The present invention relates to antiviral agents, particularly to nucleoside-based antiviral drugs, and specifically to a series of 4'-azido- and 4'-methoxy-substituted nucleosides. The invention is also directed to formulations and methods for treating viral infections in a mammal, as well as to methods of making the subject compounds.

2. Background Information

Viruses have long been known to be the cause of some of the most costly, troublesome and devastating infections to man. In recent years, this pattern has been underscored by the onset of Acquired Immune Deficiency Syndrome (AIDS), which has been found to be the result of infection by the human immunodeficiency virus (HIV).

Various active agents have been proposed for the treatment of viruses such as AIDS. Typically, these active agents have suffered from a disadvantageous therapeutic index, i.e., the ratio of activity to toxicity (in other words, their beneficial effect was outweighted by their toxic nature).

For example, the drug AZT (3'-azidothymidine) is described in European Patent Application 86307071.0; it is presently used for treatment of AIDS. It is not, however, a cure for the disease. AZT is also fairly toxic to the bone marrow, requiring patients under treatment to receive frequent blood transfusions, and although their disease symptoms are diminished and life is prolonged, AIDS related death is still considered inevitable.

Another example is the drug DDC (2',3'-dideoxycytidine), as described in PCT/US86/01626, having an international filing date of Aug. 8, 1986, claiming priority from U.S. Ser. No. 769,017, now abandoned, filed Aug. 26, 1985. This drug is currently under investigation for the treatment of HIV infection. It is more potent than AZT, but, it is also very toxic, leading often to severe peripheral neuropathy.

4'-Substituted nucleosides have been described previously [see *Ann. N.Y. Acad. Sci.*, 255, 151 (1975)]. More particularly, various 4'-methoxypurine and 4'-methoxypyrimidine ribonucleosides and 4'-azidocytidine have been synthesized and screened for their antiviral activity, but, have not shown any usefulness in this regard. For example, 4'-azidocytidine is cytotoxic and devoid of anti-HIV activity.

5-Chloro-substituted derivatives of 2',3'-didehydro-2',3'-dideoxyuridine, 3'-fluoro-2',3'-dideoxyuridine and 3'-azido-2',3'-dideoxyuridine have been described previously [see Biochemical Pharmacology, Vol 38, No. 6, pp 869–74 (1989)]. Preliminary results there report that 5-chloro-substituted-3'-fluoro-2',3'-dideoxyuridine and 5-chloro-substituted-3'-azido-2',3'-dideoxyuridine exhibit potent antiviral activity, however, further studies are required to assess their therapeutic potential.

It has remained desired to provide antiviral active agents having a high therapeutic index, such as the compounds of the present invention.

SUMMARY OF THE INVENTION

One aspect of the present invention relates to 4'-substituted-nucleosides, i.e., the compounds of Formula I:

Formula I wherein:

B is a purine or a pyrimidine;

X and X' are H, OH or F, provided that at least one is H;

Y and Y' are H, OH, OCH$_3$ or F, provided that at least one is H;

Y' and Z together form a cyclic phosphate ester, provided that Y is H; or

Z is

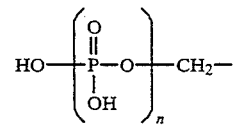

where n is zero, one, two or three; and Z' is N$_3$ or OCH$_3$;

provided that when X' and Y' are OH and Z' is N$_3$, B is not cytosine, and when X' and Y' are OH and Z' is OCH$_3$, B is not uracil, adenine or cytosine;

and the pharmaceutically acceptable esters, ethers and salts thereof.

When B of Formula I is a pyrimidine, it encompasses 5-halo-2,4-dioxo-pyrimidines, including 5-fluoro-2,4-dioxopyrimidine, 5-chloro-2,4-dioxopyrimidine, 5-bromo-2,4-dioxopyrimidine and 5-iodo-2,4-dioxopyrimidine.

In another aspect, the invention relates to a pharmaceutical composition containing a therapeutically effective amount of a compound of Formula I or a pharmaceutically acceptable ester or salt thereof admixed with at least one pharmaceutically acceptable excipient.

In still another aspect, the invention relates to a method of treating infections in a mammal by administering to a mammal in need of such treatment a therapeutically effective amount of a compound of Formula I or a pharmaceutically acceptable ester or salt thereof.

Yet another aspect of the invention relates to precursors for making the compounds of Formula I and the pharmaceutically acceptable salts and esters thereof, represented by Formula II:

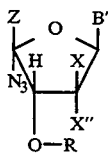

Formula II wherein:

B' is the same as B in Formula I, or an acylated equivalent thereof;

R is methyl or an acyl group such as anisoyl, benzoyl, acetyl or furan-2-carbonyl;

X is H or F;

X" is H, F, or the group —O—R; and

Z is methylene with a leaving group such as iodo or bromo;

provided that when Z' is iodomethyl and X" is —O—R and R is benzoyl, B' is not $N^4$-benzoylcytosine.

Another aspect of the invention relates to processes for making the compounds of Formula I and the pharmaceutically acceptable salts and esters thereof. For example, a compound of Formula I is made by contacting a compound of Formula II with hydrogen peroxide or a peracid (such as peroxybenzoic acid, peracetic acid, 3-chloroperoxybenzoic acid or the like) followed by a base (such as aqueous sodium hydroxide, sodium methoxide, methanolic sodium methoxide, methanolic ammonia, ammonium hydroxide, aqueous dimethylamine or the like).

DETAILED DESCRIPTION

Definitions and General Parameters

The following definitions are set forth to illustrate and define the meaning and scope of the various terms used to describe the invention herein.

The term "lower alkyl" refers to a cyclic, branched or straight chain monovalent alkyl radical of one to four carbon atoms. This term is further exemplified by such radicals as methyl, ethyl, n-propyl, isopropyl, n-butyl, t-butyl, or i-butyl.

The term "lower alkoxy" refers to the group —O—R' where R' is lower alkyl.

The term "aryl" refers to a monovalent unsaturated aromatic carbocyclic radical having a single ring (e.g., phenyl) or two condensed rings (e.g., naphthyl), which can optionally be mono-, di- or tri-substituted, independently, with hydroxy, lower alkyl, lower alkoxy, chloro, fluoro, and/or cyano.

The term "halo" refers to fluoro, bromo, chloro and iodo.

The term "heterocycle" refers to a monovalent unsaturated or aromatic carbocyclic radical having at least one hetero atom, such as N, O or S, within the ring, each available position of which can optionally be substituted, independently, with, e.g., hydroxy, oxo, amino, imino, lower alkyl, lower alkoxy, bromo, chloro, fluoro, and/or cyano. Included within this class of substituents are purines and pyrimidines.

The term "purine" refers to nitrogenous bicyclic heterocycles, typically including the naturally occurring purines adenine (or 6-aminopurine), hypoxanthine (or 6-oxopurine), guanine (2-amino-6-oxopurine) and xanthine (2,6-dioxopurine). As used herein, the term "purine" also includes moieties that have been derivatized or modified by substitution on the parent skeleton, such as, 2-aminopurine, 8-aminopurine, 2,6-diaminopurine and the like, and/or analogs wherein the parent skeleton is modified by substituting a carbon for a nitrogen or substituting a nitrogen for a carbon, such as, 9-deazapurine, 7-cyano-7-deazapurine, 8-azapurine and the like. These compounds can be of natural or synthetic origin, isolated or manufactured using exclusively or any combination of chemical, biochemical or enzymological methodology.

The term "pyrimidine" refers to nitrogenous monocyclic heterocycles, typically including the naturally occurring pyrimidines cytosine (4-amino-2-oxopyrimidine), uracil (2,4-dioxopyrimidine) and thymine (5-methyl-2,4-dioxopyrimidine). As used herein, the term pyrimidine also includes moieties that have been derivatized or modified by substitution on the parent skeleton, such as, 5-ethyl-2,4-dioxopyrimidine, 5-propyl-2,4-dioxopyrimidine, 5-fluoromethyl-2,4-dioxopyrimidine, 5-difluoromethyl-2,4-dioxopyrimidine, 5-trifluoromethyl-2,4-dioxopyrimidine, 5-(2-bromo-1-ethenyl)-2,4-dioxopyrimidine, 5-halo-2,4-dioxopyrimidine [including 5-fluoro-2,4-dioxopyrimidine, 5-bromo-2,4-dioxopyrimidine, 5-chloro-2,4-dioxopyrimidine, and 5-iodo-2,4-dioxopyrimidine] and the like, and/or analogs wherein the parent skeleton is modified by substituting a carbon for a nitrogen or substituting a nitrogen for a carbon, such as, 4-amino-5-aza-2-oxo-pyrimidine, 6-aza-5-methyl-2,4-dioxopyrimidine, 6-aza-2,4-dioxopyrimidine, 1-deaza-5-methyl-2,4-dioxo-pyrimidine and the like. These compounds can be of natural or synthetic origin, isolated or manufactured using exclusively or any combination of chemical, biochemical or enzymological methodology.

"Thymidine" is by definition 1-(2-deoxy-β-D-erythro-pentofuranosyl)thymine. Thus, by convention, the compound is not referred to as 2'-deoxythymidine even though the X' position corresponding to Formulae I and II is not OH.

The term "nucleoside" refers to a compound composed of any pentose moiety attached to the natural position of a purine (the 9-position) or pyrimidine (the 1-position) or to the equivalent position in an analog.

The term "nucleotide" refers to a phosphate ester substituted on the 5'-position of a nucleoside. A nucleotide can have one, two or three phosphoryl groups. Thus for any given nucleoside, there can be a monophosphate, diphosphate and triphosphate ester. Further, the mono-phosphoryl moiety may be linked to two positions of the penrose forming the 3'5'-cyclic phosphate.

In naming the compounds of the instant invention the following numbering systems will be used for the furanosyl ring:

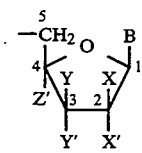

When the foregoing structure represents a nucleoside, the positions are typically referred to as the prime position (e.g., 4'), whereas the positions on the purine or pyrimidine are not.

Purines are numbered according to the following formula:

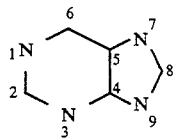

for example, representing guanine where the 2-position is NH₂ and the 6-position is =O.

Pyrimidines are numbered according to the following formula:

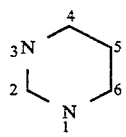

for example, representing thymine where the 2-position is =O, the 4-position is =O, and the 5-position is —CH₃.

The position of double bonds in purine and pyrimidine substituents will be apparent to those skilled in the art. It should be further understood that the substitution of a hydroxy or amino on the purine and pyrimidine ring also encompasses the tautomeric oxo or imino forms.

The 3',5'-cyclic phosphate esters are represented by the following formula:

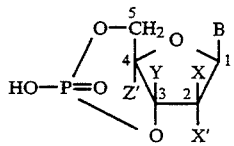

The compounds of the invention will be named using the above-shown numbering system as 4'-substituted nucleosides and derivatives. Some representative compounds are named in the following examples.

The compound of Formula I where B is thymine, X and X' are H, Y is H, Y' is OH, n is zero, and Z' is N₃, can be named: 4'-azidothymidine, or 1-(4-azido-2-deoxy-β-D-erythro-pentofuranosyl)thymine, or 1-(4-azido-2-deoxy-β-D-erythro-pentofuranosyl)-5-methyl-2,4-dioxopyrimidine.

The compound of Formula I where B is thymine, X and X' are H, Y is H, Y' is F, n is zero, and Z' is OCH₃, can be named: 3'-deoxy-3'-fluoro-4'-methoxythymidine, or 1-(2,3-dideoxy-3-fluoro-4-methoxy-β-D-erythro-pentofuranosyl)thymine, or 1-(2,3-dideoxy-3-fluoro-4-methoxy-β-D-erythro-pentofuranosyl)-5-methyl-2,4-dioxopyrimidine.

The compound of Formula I where B is 2-aminopurine, X and X' are H, Y is H, Y' is OH, n is zero, and Z' is N₃, is named 2-amino-9-(4-azido-2-deoxy-β-D-erythro-pentofuranosyl)purine.

The compound of Formula I where B is uracil, X and Y are H, X' and Y' are OH, n is zero, and Z' is N₃, can be named: 4'-azidouridine, or 1-(4-azido-β-D-ribofuranosyl)uracil, or 1-(4-azido-β-D-ribofuranosyl)2,4-dioxopyrimidine.

Certain compounds of the present invention possess asymmetric carbons and may be prepared in either optically active form, including the β-D or the α-L forms, or as a racemic mixture. Unless otherwise specified, the compounds described herein are all in the β-D-furanosyl configuration. However, the scope of the subject invention herein is not to be considered limited to this form, but to encompass all other individual optical isomers of the subject compounds and mixtures thereof.

A chemical bond indicated as ( ⟩ ) refers to the nonspecific stereochemistry of the asymmetric carbon atoms, e.g. at position 4' of the furanosyl ring (see Reaction Scheme B).

"Pharmaceutically acceptable esters" and "ethers" include those compounds of Formula I where an oxygen or a nitrogen has been modified, e.g., acylated by the addition of the group —C(=O)—W, wherein W is an alkyl group containing 1 to 20 carbon atoms including adamantyl, aryl, amino, alkylamino, dialkylamino, an alkoxy group containing 1 to 20 carbon atoms, —CH₂—O—CH₃, —CH₂—NH₂, or a group of the formula:

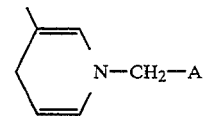

where A is hydrogen, lower alkyl or aryl [such compounds prepared in accordance with the teachings of N. Bodor, et al., Pharmac. Ther., 19, 337–386 (1983), where enhanced blood/brain barrier permeability is suggested for compounds having the subject moiety]. Particularly preferred esters are the adamantoate, the palmitoate and the dihydropyridyl esters. This invention contemplates those compounds of Formula I which are esters as described herein and at the same time are the pharmaceutically acceptable acid addition salts thereof. The invention also contemplates the isopropyl and benzyl ethers of the compounds of Formula I.

A "pharmaceutically acceptable salt" may be any salt derived from an inorganic or organic acid or base. The term "pharmaceutically acceptable anion" refers to the anion of such acid addition salts. The term "pharmaceutically acceptable cation" refers to the cation of such base addition salts. The salt, anion and/or the cation are chosen not to be biologically or otherwise undesirable.

The anions are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluensulfonic acid and the like.

The cations are derived from bases, such as alkaline earth hydroxides, including calcium hydroxide, potassium hydroxide, sodium hydroxide, lithium hydroxide and the like, preferably sodium hydroxide.

As used herein, the terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, pyridine and the like]. Unless specified to the contrary, the solvents used in the reactions of the present invention are inert organic solvents.

As used herein, the term "q.s." means adding a quantity sufficient to achieve a stated function, e.g., to bring a solution to a desired volume (e.g., 100 mL).

Unless specified to the contrary, the reactions described herein take place at atmospheric pressure over a temperature range from about −20° C. to about 100° C., more preferably from about 10° C. to about 50° C., and most preferably at about room (or "ambient") temperature, e.g., about 20° C.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

As used herein, the term "treatment" or "treating" means any treatment of a disease in a mammal, including:

(i) preventing the disease, that is, avoiding any clinical symptoms of the disease;

(ii) inhibiting the disease, that is, arresting the development or progression of clinical symptoms; and/or (iii) relieving the disease, that is, causing the regression of clinical symptoms.

As used herein, the term "effective amount" means a dosage sufficient to provide treatment for the disease state being treated. This will vary depending on the patient, the disease and the treatment being effected.

Synthesis of the Compounds of Formula I

As used in the Reaction Schemes, the substituents B, B', R, X, X', X'', Y, Y', Z, Z' and n are the same as described in the Summary of the Invention.

The compounds of Formula I where Y' is OH and Z' is azido are prepared as described with reference to Reaction Scheme A.

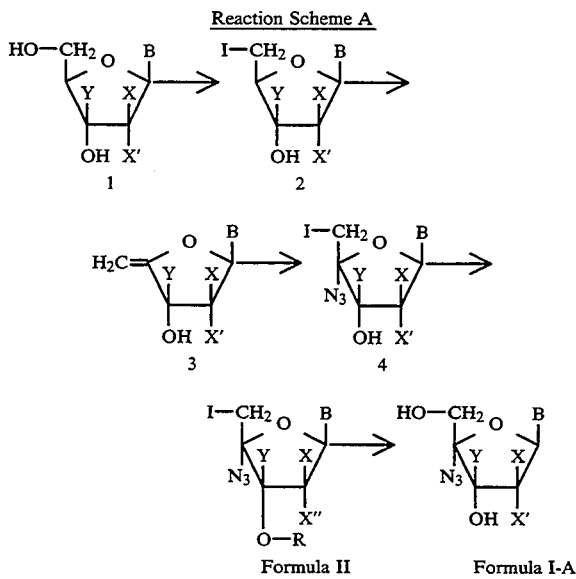

Starting Materials

Referring to Reaction Scheme A, the starting materials of Formula 1 are 2'-deoxy-erythro-pentofuranosyl nucleosides, ribofuranosyl nucleosides and arabinofuranosyl nucleosides selected from the compounds where B is, for example, 6-aminopurine, 2-amino-6-oxopurine, 2,4-dioxopyrimidine, 5-methyl-2,4-dioxopyrimidine, 4-amino-2-oxopyrimidine, 2,6-diaminopurine, 6-aminopurine, 8-aminopurine, 5-ethyl-2,4-dioxopyrimidine, 5-propyl-2,4-dioxopyrimidine, 5-(2-bromo-1-ethenyl)-2,4-dioxopyrimidine, 5-fluoro-2,4-dioxopyrimidine, 5-fluoromethyl-2,4-dioxopyrimidine, 5-difluoromethyl-2,4-dioxopyrimidine, 5-trifluoromethyl-2,4-dioxopyrimidine, 5-chloro-2,4-dioxo pyrimidine, 5-bromo-2,4-dioxopyrimidine and 5-iodo-2,4-dioxopyrimidine. Many of these materials are available commercially from such suppliers as, Aldrich Chemical Company or Sigma Chemical Company; and where not, they can be easily prepared according to procedures that are well known to the art and published in the literature.

Preparation of Intermediate 2

Referring to Reaction Scheme A, a compound of Formula 1 is iodinated using a mixture of triphenylphosphine, iodine and pyridine, or similar iodinating reagents such as methyltriphenoxyphosphonium iodide, in a solvent (such as dioxane, tetrahydrofuran, or dichloromethane). After keeping the mixture at a temperature between room temperature and about 50° C., preferably at about room temperature, for a period from about 4 hours to 16 hours, preferably about 8 hours; an intermediate of Formula 2 is isolated by evaporation of the solvents and extraction of the residue, followed by either crystallization or chromatography.

Preparation of Intermediate 3

A compound of Formula 2 is dissolved or suspended in a solvent (such as methanol or other alcohol, or dioxane, tetrahydrofuran, dimethylformamide, dimethylsulfoxide; preferably methanol) by the addition of a base (such as sodium methoxide, potassium t-butoxide or the like; preferably sodium methoxide). The solution is heated at a temperature from about 50° C. to about 100° C., preferably about 65° C.; for a period of about 12 hours to 24 hours, preferably about 16 hours. After neutralizing with an acid (such as acetic acid), the solvents are removed by evaporation and a compound of Formula 3 is crystallized out of the residue or isolated by chromatography.

Alternatively, a compound of Formula 3 can be prepared by dissolving compound of Formula 2 in a solvent (such as dimethylformamide, dimethylsulfoxide, N-methyl-2-pyrrolidone or the like) and adding a base (such as 1,8-diazabicyclo[5.4.0]undec-7-ene or 1,5-diazabicyclo[4.3.0]non-5-ene) and keeping the mixture at about room temperature for a period of about 12 hours to 24 hours, preferably about 16 hours. After removal of the solvent by evaporation, the compound of Formula 3 is purified by chromatography.

Preparation of Intermediate 4

A compound of Formula 4 is prepared by adding a solution of compound of Formula 3 (in dimethylformamide or N-methyl-2-pyrrolidone or the like; preferably DMF) to a mixture of an alkaline metal azide (such as sodium or lithium azide, preferably sodium azide) and an iodinating agent (such as iodine monochloride or iodine, preferably iodine monochloride) in solution preferably with the same solvent. After stirring the mixture for a period of about 5 minutes to 2 hours, preferably about 1 hour; at a temperature range of about 0° C. to 50° C., preferably at about room temperature;

the compound is isolated by extraction, optionally followed by chromatography or by crystallization.

Preparation of Compounds of Formula II

A solution of a compound of Formula 4 and an acid chloride or anhydride (such as benzoyl chloride, anisoyl chloride, acetic anhydride, or the like) in a solvent (such as pyridine) is kept at a temperature range of 20° C. to 50° C., preferably at about room temperature; for a period of 6 hours to 24 hours, preferably for about 16 hours. The compound of Formula II is recovered by evaporation of the solvent and purified by chromatography or by crystallization.

Preparation of Compounds of Formula I

A compound of Formula II is dissolved or suspended in a solvent such as dichloromethane saturated with water and treated with an oxidizing agent (such as a carboxylic peroxy acid, e.g., peroxybenzoic acid, peracetic acid, 3-chloroperoxybenzoic acid or the like). The reaction by-products are removed by extraction and the residue is treated with a base (such as, aqueous sodium hydroxide, sodium methoxide, methanolic sodium methoxide, methanolic ammonia, ammonium hydroxide, aqueous dimethylamine or the like). The compound of Formula I-A is isolated by evaporation of the solvent and purification, for instance, by chromatography.

Compounds of Formula I-A prepared by the above-described process of the invention may be identified by the presence of a detectable amount of Formula II or the salt or the acid derived from the peroxy acid used in the reaction. While it is well known that pharmaceuticals must meet pharmacopoeia standards before approval and/or marketing, and that precursors (such as Formula II) or side products (such as the acids or salts) should not exceed the limits prescribed by pharmacopoeia standards, final compounds prepared by a process of the present invention may have minor, but detectable, amounts of such materials present, for example at levels in the range of 1 part per million to two percent. These levels can be detected, e.g., by HPLC-mass spectrometry. It is important to monitor the purity of pharmaceutical compounds for the presence of such materials, whose presence is additionally disclosed as a method of detecting use of a process of the invention.

The compounds of Formula I, particularly where Y' is OH and Z' is methoxy, are prepared as described with reference to Reaction Scheme B.

Reaction Scheme B

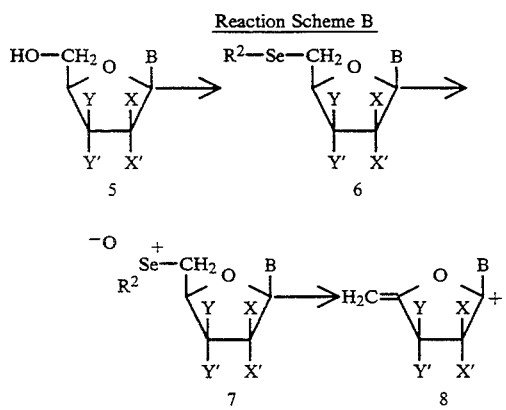

-continued
Reaction Scheme B

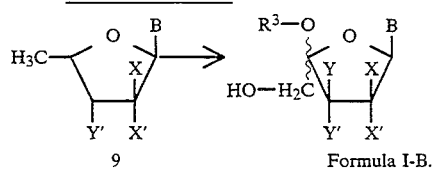

Starting Materials

Referring to Reaction Scheme B, the starting materials of Formula 5 are 2'-deoxy-erythro-pentofuranosyl nucleosides, ribofuranosyl nucleosides and arabinofuranosyl nucleosides selected from the compounds where B is, for example, 6-aminopurine, 2-amino-6-oxopurine, 2,4-dioxopyrimidine, 5-methyl-2,4-dioxopyrimidine, 4-amino-2-oxopyrimidine, 2,6-diaminopurine, 6-aminopurine, 8-aminopurine, 5-ethyl-2,4-dioxopyrimidine, 5-propyl-2,4-dioxopyrimidine, 5-(2-bromo-1-ethenyl)-2,4-dioxopyrimidine, 5-fluoro-2,4-dioxopyrimidine, 5-fluoromethyl-2,4-dioxopyrimidine, 5-difluoromethyl-2,4-dioxopyrimidine, 5-trifluoromethyl-2,4-dioxopyrimidine, 5-bromo-2,4-dioxopyrimidine, 5-chloro-2,4-dioxopyrimidine and 5-iodo-2,4-dioxopyrimidine. Many of these materials are available commercially from such suppliers as, Aldrich Chemical Company or Sigma Chemical Company; and where not, they can be easily prepared according to procedures that are well known to the art and published in the literature. For example, see *Synthetic Procedures in Nucleic Acid Chemistry*, Vol. 1, Zorbach and Tipson, Eds., Wiley Interscience (1968); and *Nucleic Acid Chemistry*, parts 1–3, Townsend and Tipson, Eds., Wiley Interscience (1978, 1978, 1986).

Preparation of Intermediate 6

A compound of Formula 5 is reacted with a selenating agent (such as, an aryl selenyl halide or selenocyanate; preferably o-nitrophenylselenocyanate) in the presence of a phosphine (e.g. triphenylphosphine, tri-n-butylphosphine) in a solvent (such as tetrahydrofuran, dichloromethane, or dioxane). After keeping the reaction at a temperature from about 0° C. and 50° C., preferably at about room temperature for a period of about 30 minutes to about 24 hours, preferably about 1 hour, the compound of Formula 6 is isolated following extraction, evaporation and purification, e.g. chromatography.

Preparation of Intermediate 7

A compound of Formula 6 is dissolved or suspended in a solvent (such as dichloromethane, chloroform or the like) and treated with an oxidizing agent (such as hydrogen peroxide or a carboxylic peracid, e.g., peroxybenzoic acid, 3-chloroperoxybenzoic acid, peracetic acid or the like). Optionally a neutralizing agent (such as sodium bicarbonate or the like) may be added. The reaction mixture is stirred at a temperature between about 0° C. and 50° C., preferably at about room temperature, for a period of about 5 minutes to about 24 hours, preferably for 30 minutes. The compound of Formula 7 is isolated following extraction and evaporation followed optionally by purification on silica gel or the like. Preferably, the compound of Formula 7 is converted directly to a compound of Formula 8 without purification.

Preparation of Intermediates 8 and 9

A compound of Formula 7 is heated in a solvent (such as toluene, benzene or the like) in the presence of a base (such as a trialkyl or triarylamine, preferably triethylamine) to a temperature in the range of about 50° C. to 150° C. for a period of about 10 minutes to about 5 hours, preferably about 1 hour. The compound of Formula 8 is isolated following evaporation and purification and optionally crystallization. Depending on the nature of the substituents Y and Y', the isomeric compound of Formula 9 may also be isolated from the reaction mixture.

Preparation of Compounds of Formula I-B

A compound of Formula 8 is reacted with a peracid (such as peroxybenzoic acid, 3-chloroperoxybenzoic acid, peracetic acid or the like) in the presence of an alcohol solvent (such as, a primary lower alkyl alcohol, preferably methanol, ethanol or the like). The solution is stirred at a temperature between about −40° C. to 50° C., for a period of a few minutes to about 48 hours, depending on the Y' group. For instance, if Y' is H then the solution is stirred preferably at a temperature between −10° C. to 0° C. for about 1 to 2 minutes; if Y' is F then the solution is stirred preferably at about room temperature for about 1 hour to about 48 hours. Compounds of Formula I-B (where $R^3$ is a lower alkyl group corresponding to the primary lower alkyl alcohol used in the reaction) are isolated following extraction, evaporation and crystallization; optionally purification by chromatography may be employed.

Other compounds of Formula I can be prepared from the compounds of Formula 3 in Reaction Scheme A, as described with reference to Reaction Scheme C. As used in Reaction Scheme C, $R^5$ is a tri-substituted silyloxy group.

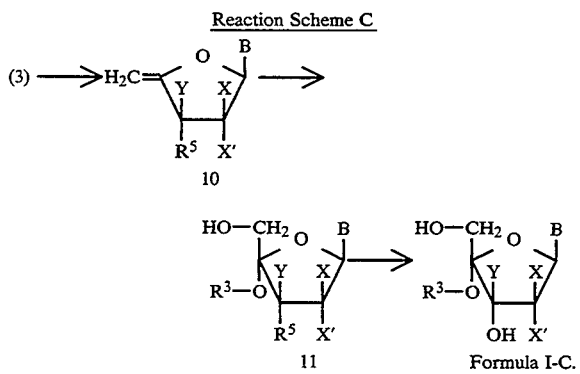

Preparation of Intermediate 10

A compound of Formula 3, prepared, e.g., as described with reference to Reaction Scheme A, is treated with a silylating reagent (e.g., a tri-substituted silyl chloride, such as trimethylsilyl chloride, t-butyldimethylsilyl chloride or the like) in a solvent (such as dichloromethane, chloroform, tetrahydrofuran, dimethylformamide, dioxane or the like); and in the presence of a base (such as triethylamine, pyridine, imidazole or the like); at a temperature in the range of about 0° C. to 60° C., preferably at room temperature, for a period from about 10 minutes to about 10 hours, preferably for about 3 hours. The compound Formula 10 is isolated by evaporation, extraction and optionally after chromatographic purification.

Preparation of Intermediate 11

A compound of Formula 10 is reacted with a peracid (such as peroxybenzoic acid, 3-chloroperoxybenzoic acid, peracetic acid or the like) in the presence of an alcohol solvent (such as, a primary lower alkyl alcohol, preferably methanol, ethanol or the like). The solution is stirred at a temperature between about −40° C. to 50° C., for a period of a few minutes to about 48 hours, preferably at about room temperature for about 2 hours. The compound of Formula 11 (where $R^3$ is a lower alkyl group corresponding to the primary lower alkyl alcohol solvent) is isolated following extraction, evaporation and crystallization; optionally purification by chromatography may be employed.

Preparation of Compounds of Formula I-C

A compound of Formula 11 is dissolved in a solvent (such as dichloromethane, chloroform, THF, toluene or the like) and deprotected by contacting it with a source of fluoride ion (such as hydrogen fluoride-pyridine, cesium fluoride, tetrabutylammonium fluoride or the like), at a temperature from about 0° C. to about 50° C., for about 5 minutes to about 4 hours, preferably about 1 hour, to give a compound of Formula I-C.

Other 4'-azido compounds of Formula I can be prepared starting from the 4'-methoxy compounds (for example, the compounds of Formula I-B made as shown in Reaction Scheme B) as described with reference to Reaction Scheme D.

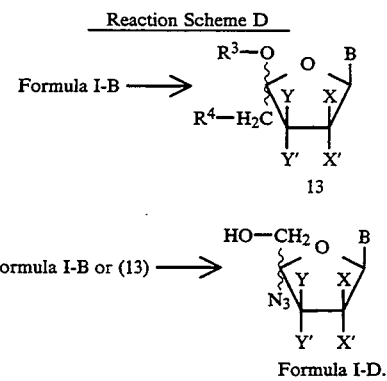

Preparation of Intermediate 13

A compound of Formula I-B is treated with a silylating reagent (e.g., a tri-substituted silyl chloride, such as trimethylsilyl chloride, t-butyldimethylsilyl chloride or the like) in a solvent (such as dichloromethane, chloroform, tetrahydrofuran, dimethylformamide, dioxane or the like); and in the presence of a base (such as triethylamine, pyridine, imidazole or the like); at a temperature in the range of about 0° C. to 60° C., preferably at room temperature, for a period from about 10 minutes to about 10 hours, preferably for about 3 hours. The compound Formula 13 (where $R^3$ is lower alkyl, and any of X, X', Y or Y' that was OH in Formula I-B is optionally $R^4$, and $R^4$ is a trisubstituted silyloxy group) is isolated by evaporation, extraction and optionally chromatography.

Preparation of Formula I-D

Compounds of Formula I-B or Formula 13 are converted to a compound Formula I-D by dissolving a compound of Formula I-B or Formula 13 in a solvent (such as dichloromethane, chloroform or the like) and treating it with an azide (such as, azidotrimethylsilane, sodium azide, lithium azide, or the like) in the presence of a Lewis acid catalyst (such as trimethylsilyl trifluoromethanesulfonate, triisopropylsilyl trifluoromethanesulfonate, or the like) at a temperature in the range of about 0° C. to about 100° C., preferably at room temperature; for a period of 10 minutes to 100 hours, preferably 24 to 50 hours. The compound of Formula I is isolated by evaporation, optionally treating it with an aqueous base or fluoride. Finally, optional extraction is followed by purification such as silica gel chromatography and crystallization.

Preparation of Formula I Where B is a 5-Halo-2,4-dioxopyrimidine

4'-Azido-2'-deoxyuridine is acetylated at the 3' and 5' positions of the uridine by contacting it with an acetylating agent, such as acetic anhydride in the presence of pyridines, such as 4-dimethylaminopyridine and pyridine, by stirring at room temperature. The resulting 4'-azido-3',5'-di-0-acetyl-2'-deoxyuridine is put into solution, for example in anhydrous pyridine, glacial acetic acid or methanol, and contacted with a halogenating agent such as a N-halosuccinimide (e.g., N-chlorosuccinimide or N-bromosuccinimide) or a halo monochloride (such as iodine monochloride) at elevated temperature, such as 75° to 125° C., preferably about 100° C., or at the reflux temperature of the solvent system used, for a period of about 10 minutes to about 5 hours, preferably about 30 minutes. The reaction mixture is cooled to ambient temperature for an added period of about 2 to 10 hours, preferably about 5 hours, and the halogenated product is isolated.

Preparation of the Phosphate Salts of Formula I

Phosphorylating agents useful for preparation of the phosphate salts include, for example, phosphoryl chloride, pyrophosphoryl chloride and the like, as will be known to those skilled in the art.

The 5'-monophosphate esters of the nucleosides described herein are prepared starting from the parent nucleoside, for example, using methods described by Imai et al., *Journal of Organic Chemistry*, 34, 1547 (1969).

The 5'-diphosphate esters and 5'-triphosphate esters of the nucleosides described herein are prepared starting from the monophosphates, for example, using methods described by Hoard et al., *Journal of the American Chemical Society*, 87, 1785 (1965).

The 3',5'-cyclicphosphate esters of the nucleosides described herein are prepared starting from the monophosphates, for example, using methods described in Smith et al., *Journal of the American Chemical Society*, 83, 698 (1961).

Preparation of the Salts of Formula I

The pharmaceutically acceptable salts of Formula I are prepared by dissolving a compound of Formula I in a suitable solvent (such as water) adding one to three molar equivalents (preferably one molar equivalent) of an appropriate acid (such as hydrochloric acid) or base (such as an alkaline earth hydroxide, e.g., lithium hydroxide, calcium hydroxide, potassium hydroxide, sodium hydroxide or the like; preferably sodium hydroxide) and stirring. The salt is isolated by lyophilization or by precipitation, using techniques that will be apparent to those skilled in the art.

Preparation of the Esters of Formula I

The pharmaceutically acceptable esters of Formula I are prepared by adding a compound of Formula I and a catalyst (such as 4-dimethylaminopyridine) in pyridine, dropwise to an appropriate acid chloride of the acyl group to be added (such as adamantanecarboxylic acid chloride, palmitic acid chloride, N-methyl-dihydropyrid-3-ylcarboxylic acid chloride or isopropyl acid chloride) either neat or in a solvent (such as methylene chloride, dichloroethane or the like). The reactants are stirred at room temperature for 10 to 24 hours, preferably from 12 to 18 hours. The product is isolated by methods well known in the art such as chromatography.

Preferred Processes and Last Steps

The compounds of the present invention can be prepared according to the following last steps (in which non-essential substituents are not discussed, but, will be apparent to those skilled in the art from reference to the foregoing reaction schemes):

a 4'-azido-5'-deoxy-5'-iodonucleoside is contacted with an acyl halide to give a compound according to Formula II;

a 3'-0-acyl-4'-azido-2',5'-dideoxy-5'-iodonucleoside or a 2',3'-di-0-acyl-4'-azido-5'-deoxy-5'-iodonucleoside is contacted with a peracid followed by a base to give a compound according to Formula I;

a 1-(3-0-p-anisoyl-4-azido-2,5-dideoxy-5-iodo-$\beta$-D-erythro-pentofuranosyl)5-halo-2,4-dioxopyrimidine is contacted with a peroxy acid to give the a compound according to Formula I where B is a 5-halo-2,4-dioxopyrimidine;

a 3',5'-dideoxy-3'-fluorothymidin-4'-ene is contacted with a peracid in methanol to give 3'-deoxy-3'-fluoro-4'-methoxythymidine;

a (5-deoxy-$\beta$-D-ribo-pent-4'-enofuranosyl)nucleoside, or a (2,5-dideoxy-$\beta$-D-erythro-pent-4'-enofuranosyl)nucleoside, or a (2,3,5-trideoxy-$\beta$-pent-4'-enofuranosyl)nucleoside, is contacted with a peracid in methanol to give a compound according to Formula I where Z' is methoxy;

a 3'-0-tri-substituted silyl-4'-methoxy-2'-deoxynucleoside or a 2',3'-di-O-tri-substituted silyl-4'-methoxynucleoside is contacted with a source of fluoride ion to give a compound according to Formula I where Z' is methoxy;

a compound of Formula I where Z' is methoxy is contacted with an azide in the presence of a Lewis acid catalyst to give a compound according to Formula I where Z' is azido;

a 2',3',5'-trideoxynucleosid-4'-ene is contacted with a peracid in methanol to give a compound of Formula I where Z' is methoxy.

a 2',3'-dideoxy-4'-alkoxynucleoside is contacted with an azide in the presence of a Lewis acid catalyst to give a compound according to Formula I where Z' is azido;

a compound of Formula I where n is zero is contacted with a phosphorylating agent to give a compound according to Formula I where n is one;

a compound of Formula I where n is one is contacted with a phosphorylating agent to give a compound according to Formula I where n is two;

a compound of Formula I where n is one is contacted with a phosphorylating agent to give a compound according to Formula I where n is three;

a 4'-azido-3',5'-di-0-acetyl-2'-deoxyuridine is contacted with a halogenating agent to give a compound of Formula I where B is a 5-halo-2,4-dioxopyrimidine;

a compound of Formula I where n is one is contacted with a cyclizing agent (such as dicyclohexylcarbodiimide) to give a compound according to Formula I where Y' and Z together form a cyclic phosphate ester;

a compound of formula I, following protection of reactive nitrogen atoms on the purine or pyrimidine heterocycle by acylation (e.g., benzoylation), is reacted with a strong base (e.g., sodium hydride) followed by addition of an alkyl halide (such as benzyl bromide or 2-iodopropane) to give the corresponding ether compound of Formula I after deacylation;

a compound of Formula I is contacted with a pyridine catalyst and an acid chloride to give the corresponding ester;

a compound of Formula I is contacted with a pharmaceutically acceptable acid to form the corresponding acid addition salt of Formula I;

a compound of Formula I is contacted with a pharmaceutically acceptable base to form the corresponding base addition salt of Formula I;

substituting a pharmaceutically acceptable acid addition salt of Formula I with another pharmaceutically acceptable acid;

substituting a pharmaceutically acceptable base addition salt of Formula I with another pharmaceutically acceptable base;

contacting an acid addition salt of Formula I with a base to form the corresponding free base compound of Formula I; and contacting an base addition salt of Formula I with a acid to form the corresponding free acid compound of Formula I.

Preferred Compounds

Presently preferred are the compounds of Formula I where B is adenine, guanine, hypoxanthine, uracil, thymine, cytosine, 2,6-diaminopurine, 2-aminopurine, 8-aminopurine, 5-ethyl-2,4-dioxopyrimidine, 5-propyl-2,4-dioxopyrimidine, 5-(2-bromo-1-ethenyl)-2,4-dioxopyrimidine, or 5-halo-2,4-dioxopyrimidine [including 5-fluoro-2,4-dioxopyrimidine, 5-chloro-2,4-dioxopyrimidine, 5-bromo-2,4-dioxo-pyrimidine, and 5-iodo-2,4-dioxopyrimidine]; especially the compounds where B is adenins, guanine, uracil, thymine, or cytosine.

Also preferred are the compounds of Formula I where Z' is azido, Y is H, X is H, and X' is H;

particularly the compounds where Y' is OH and B is thymine, uracil, cytosine, guanine or adenine;

and also the compound where Y' is H and B is thymine.

Similarly preferred are the compounds of Formula I where Z' is methoxy, X is H, X' is H, and Y is H;

particularly where Y' is F and B is thymine; and also where Y' is OH.

Still other preferred compounds of Formula I are those where B is thymine.

Most preferred are the compounds 4'-azidothymidine and 3'-fluoro-4'-methoxythymidine, especially 4'-azidothymidine.

Utility, Testing and Administration

General Utility

The compounds of this invention are particularly useful for treating viral, bacterial and fungal infections.

Generally, the infections treated with the compounds of the present invention are found in mammals, including: animals such as mice, monkeys and the like; and particularly humans.

The compounds of the present invention, including the pharmaceutically acceptable salts and esters thereof, and the compositions containing them are useful as potent antiviral agents, particularly against human immunodeficiency virus (HIV).

Testing

In vitro testing for antiviral activity against HIV is done, for example, by the procedures described by Chen et al., *Biochemical Pharmacology*, 36 (24), 4361–4362 (1987), or modifications thereof.

Inhibition of reverse transcriptase and human polymerase is determined by the procedures described by Chen et al., *Molecular Pharmacology*, 25, 441–445 (1984), or as described by Wang et al., *Biochemistry*, 21, 1597–1608 (1982), or by modifications thereof.

Tests for toxicity can be carried out by the procedures described by Diainiak, et al., *British Journal of Haematology*, 69, 229–304 (1988), or as described by Sommadossi, et al., *Agents and Chemotherapy*, 31 (3), 452–454 (1987), or by modifications thereof.

In vivo testing to demonstrate the described antiviral activity of the present compounds is done, for example, by procedures described by Jones et al., *Journal of Virology*, 62 (2), 511–518 (1988), or by modifications thereof.

Administration

The compounds of this invention are administered at a therapeutically effective dosage, i.e., a dosage sufficient to provide treatment for the disease states previously described. Administration of the active compounds and salts described herein can be via any of the accepted modes of administration for agents that serve similar utilities.

Generally, an acceptable daily dose is of about 0.01 to 150 mg per kilogram body weight of the recipient per day, preferably about 1.5 to 75 mg per kilogram body weight per day, and most preferably about 5 to 30 mg per kilogram body weight per day. Thus, for administration to a 70 kg person, the dosage range would be about 0.7 mg to 10.5 g per day, preferably about 350 mg to 2.1 g per day.

Administration can be via any accepted systemic or local route, for example, via parenteral, oral (particularly for infant formulations), intravenous, nasal, transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient and an active compound of Formula I and, in addition, may include other medicinal agents, pharmaceutical agents, carriers, adjuvants, etc.

For example, in methods of treating AIDS infections, particularly where the compromised subject is suffering from other viral infections, such as, herpes, an active compound of Formula I can be co-administered with one or more agents active in reducing viral infections, such as, acyclovir, ganciclovir, and foscarnet which have been demonstrated to reduce the severity of herpetic viral infections. Co-administration can be in the form of a single formulation (combining, for example, a compound of Formula I and ganciclovir with pharmaceutically acceptable excipients, optionally segregating the two active ingredients in different excipient mixtures designed to independently control their respective release rates and durations) or by independent administration of separate formulations containing the active agents.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a compound of Formula I. The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

Intravenous Administration

Intravenous injection has proven to be an important route of administration for antiviral agents. The compounds of the present invention can be administered via this route, for example, by dissolving the compound, salt, ester or ether in a suitable solvent (such as water or saline) or incorporation in a liposomal formulation followed, by dispersal into an acceptable infusion fluid. A typical daily dose of a compound of the invention can be administered by one infusion, or by a series of infusions spaced over periodic intervals.

Oral Administration

Oral administration can be used to deliver the compound of Formula I using a convenient daily dosage regimen which can be adjusted according to the degree of affliction or for renal impairment, or to compensate for the toxic effects of other medications administered contemporaneously. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/wt % and 99.99 wt/wt % of the compound of Formula I, but preferably such compositions will contain between 25 wt/wt % and about 80 wt/wt %.

Preferably the compositions will take the form of a capsule, pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like. For oral administration to infants, a liquid formulation (such as a syrup or suspension) is preferred.

Liposomal Formulations

Pharmaceutical formulations based on liposomes have recently reached human clinical trials. Their benefits are believed related to favorable changes in tissue distribution and pharmacokinetic parameters that result from liposome entrapment of drugs, and may be applied to the compounds of the present invention by those skilled in the art.

The formulations can be designed to either target drug to disease sites [see: Lopez-Berestein et al., *J. Infect. Dis.*, 151:704–710 (1985); Gotfredsen et al., *Biochemical Pharmacology*, 32: 3389–3396 (1983)]; or to the reticuloendothelial system [see Eppstein et al., *Int J. Immunotherapy*, 2: 115–126 (1986)], to increase duration of drug action [see: Gabizon et al., *Cancer Res.*, 42: 4734 (1982); Eppstein et al., *Delivery Systems for Peptide Drugs*, Eds. S. S. Davis, L. Ilium and E. Tomlinson, Plenum Pub. Corp., New York, pp. 277–283; C. A. Hunt, *Biochemica et Biophysica Acta.*, 719: 450–463 (1982); and Senior et al., *Biochemica et Biophysica Acta.*, 839: 1–8 (1985)], or to divert a drug away from organs that are particularly sensitive to its toxic effects [see: Weinstein et al., *Pharmac. Ther.*, 24: 207–233 (1983); Olson et al., *Eur. J. Cancer Clin. Oncol.*, 18: 167–176 (1982); and Gabzion et al., supra].

Controlled release liposomal liquid pharmaceutical formulations for injection or oral administration are described in U.S. Pat. No. 4,016,100. Liposomal applications for oral drug delivery of a lyophilized liposome/peptide drug mixture filled into intestine capsules have also been suggested, see U.S. Pat. No. 4,348,384. Additionally, viral infections of the eye (such as herpetic keratitis and HIV retinitis) may be treated by use of a sustained release drug delivery system as described in U.S. Pat. No. 4,217,898. The foregoing are incorporated herein by reference.

Suppositories

For systemic administration via suppository, traditional binders and carriers include, for example, polyalkaline glycol or triglycerides [e.g., PEG 1000 (96%) and PEG 4000 (4%)]. Such suppositories may be formed from mixtures containing active ingredients in the range of from about 0.5 wt/wt % to about 10 wt/wt %; preferably from about 1 wt/wt % to about 2 wt/wt %.

Liquids

Liquid pharmaceutically administerable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

EXAMPLES

The following preparations and examples are given to enable those skilled in the art to more clearly understand and to practice the present invention. They should not be considered as limiting the scope of the invention, but merely as being illustrative and representative thereof.

Preparation 1

1A. Formula 2 Where B is Thymine, X, X' and Y are H

To a suspension of thymidine (0.968 g, 4.0 mM) in dioxane (20 mL) containing pyridine (0.65 mL, 8.0 mM) was added triphenylphosphine (1.57 g, 6.0 mM) and iodine (1.52 g, 6.0 mM). After stirring the mixture for 7 hours at 21° C., methanol (1.0 mL) was added, followed by removal of the solvent by evaporation. A solution of the residue in ethyl acetate (150 mL) was extracted successively with water (30 mL), 10% aqueous sodium thiosulfate solution (30 mL), and brine (30 mL). The ethyl acetate phase was concentrated in vacuo to a sirup which was taken up in hot ethanol (50 mL) and filtered. The filtrate was concentrated to a volume of 15 mL. On cooling, 5'-deoxy-5'-iodothymidine crystallized out. The crystals were filtered, rinsed with ethyl acetate, and dried, affording 5'-deoxy-5'-iodothymidine (0.806 g), a compound according to Formula 2.

1B. Formula 2 Varying B and X'

By following the procedure of part A and substituting for thymidine with the following:
2'-deoxyadenosine,
2'-deoxyguanosine,
2'-deoxyuridine,
2'-deoxycytidine,
uridine,
9-(2-deoxy-β-D-erythro-pentofuranosyl)2,6-diaminopurine,
1-(2-deoxy-β-D-erythro-pentofuranosyl)5-trifluoromethyl-2,4-dioxopyrimidine,
9-(2-deoxy-β-D-erythro-pentofuranosyl)2-aminopurine,
1-(2-deoxy-β-D-erythro-pentofuranosyl)-5-fluoro-2,4-dioxopyrimidine,
1-(2-deoxy-β-D-erythro-pentofuranosyl)-5-chloro-2,4-dioxopyrimidine,
1-(2-deoxy-β-D-erythro-pentofuranosyl)-5-bromo-2,4-dioxopyrimidine, and
1-(2-deoxy-β-D-erythro-pentofuranosyl)-5-iodo-2,4-dioxopyrimidine;
there are obtained the following respective compounds:
2',5'-dideoxy-5'-iodoadenosine,
2',5'-dideoxy-5'-iodoguanosine,
2',5'-dideoxy-5'-iodouridine,
2',5'-dideoxy-5'-iodocytidine,
5'-deoxy-5'-iodouridine,
9-(2,5-dideoxy-5-iodo-β-D-erythro-pentofuranosyl)2,6-diaminopurine,
1-(2,5-dideoxy-5-iodo-β-D-erythro-pentofuranosyl)5-trifluoromethyl-2,4-dioxopyrimidine,
9-(2,5-dideoxy-5-iodo-β-D-erythro-pentofuranosyl)2-aminopurine,
1-(2,5-dideoxy-5-iodo-β-D-erythro-pentofuranosyl)5-fluoro-2,4-dioxopyrimidine,
1-(2,5-dideoxy-5-iodo-β-D-erythro-pentofuranosyl)5-chloro-2,4-dioxopyrimidine,
1-(2,5-dideoxy-5-iodo-β-D-erythro-pentofuranosyl)5-bromo-2,4-dioxopyrimidine, and
1-(2,5-dideoxy-5-iodo-β-D-erythro-pentofuranosyl)5-iodo-2,4-dioxopyrimidine.

Preparation 2

2A. Formula 3 Where B is Thymine, X, X' and Y are H

A 1N solution of sodium methoxide in methanol (0.85 mL) was added to a suspension of 5'-deoxy-5'-iodothymidine (100 mg, 0.284 mM), prepared, e.g., as described in Preparation 1A, in anhydrous methanol (5 mL). The solution was heated at reflux for 16 hours, cooled to room temperature, and neutralized by the addition of glacial acetic acid. After removal of solvents by evaporation, the residue was crystallized from ethanol to give 58 mg of 5'-deoxythymidin-4'-ene (a compound according to Formula 3) (mp 208°–210° C.).

2B. Formula 3 Varying B and X'

By following the procedure of part A and substituting for 5'-deoxy-5'-iodothymidine the following:
2',5'-dideoxy-5'-iodoadenosine,
2',5'-dideoxy-5'-iodoguanosine,
2',5'-dideoxy-5'-iodouridine,
2',5'-dideoxy-5'-iodocytidine,
5'-deoxy-5'-iodouridine,
9-(2,5-dideoxy-5-iodo-β-D-erythro-pentofuranosyl)2,6-diaminopurine,
1-(2,5-dideoxy-5-iodo-β-D-erythro-pentofuranosyl)5-trifluoromethyl-2,4-dioxopyrimidine,
9-(2,5-dideoxy-5-iodo-β-D-erythro-pentofuranosyl)2-aminopurine,
1-(2,5-dideoxy-5-iodo-β-D-erythro-pentofuranosyl)5-fluoro-2,4-dioxopyrimidine,
1-(2,5-dideoxy-5-iodo-β-D-erythro-pentofuranosyl)5-chloro-2,4-dioxopyrimidine,
1-(2,5-dideoxy-5-iodo-β-D-erythro-pentofuranosyl)5-bromo-2,4-dioxopyrimidine, and
1-(2,5-dideoxy-5-iodo-β-D-erythro-pentofuranosyl)-5-iodo-2,4-dioxopyrimidine;
there are obtained the following respective compounds:
2'5'-dideoxyadenosin-4'-ene,
2'5'-dideoxyguanosin-4'-ene,
2'5'-dideoxyuridin-4'-ene,
2'5'-dideoxycytidin-4'-ene,
5'-deoxyuridin-4'-ene,
9-(2,5-dideoxy-S-D-erythro-pent-4-enofuranosyl)2,6-diaminopurine,
1-(2,5-dideoxy-β-D-erythro-pent-4-enofuranosyl)5-trifluoromethyl-2,4-dioxopyrimidine,
9-(2,5-dideoxy-β-D-erythro-pent-4-enofuranosyl)2-aminopurine,
1-(2,5-dideoxy-β-D-erythro-pent-4-enofuranosyl)5-fluoro-2,4-dioxopyrimidine,
1-(2,5-dideoxy-β-D-erythro-pent-4-enofuranosyl)5-chloro-2,4-dioxopyrimidine,
1-(2,5-dideoxy-β-D-erythro-pent-4-enofuranosyl)5-bromo-2,4-dioxopyrimidine, and
1-(2,5-dideoxy-β-D-erythro-pent-4-enofuranosyl)5-iodo-2,4-dioxopyrimidine.

Preparation 3

3A. Formula 4 Where B is Thymine, X, X' and Y are H

To a stirred suspension of sodium azide (8.70 g, 134 mM) in dimethylformamide (60 mL), under nitrogen, was added iodine monochloride (10.8 g, 67 mM). After 20 min, a solution of 5'-deoxythymidin-4'-ene (6.00 g, 26.8 mM), prepared, e.g., as described in Preparation 2, in dimethylformamide (600 mL) was added dropwise over 30 min. The mixture was allowed to stir at 21° C. for an additional hour. Saturated aqueous sodium bicarbonate was added (200 mL) followed by enough saturated aqueous sodium thiosulfate solution to render the mixture colorless. The mixture was filtered and the filtrate was evaporated to an oil. A solution of the oil in H$_2$O (300 mL) was extracted four times with ethyl acetate (250 mL portions). The combined organic extracts were dried (MgSO$_4$), and the solvent removed by evaporation to give 4'-azido-5'-deoxy-5'-iodothymidine (a compound according to Formula 4) as 12 g of viscous sirup of sufficient purity for subsequent reactions.

3B. Formula 4.Varying B and X'

By following the procedure of part A and substituting for thymidin-4'-ene the following:
2'5'-dideoxyadenosin-4'-ene,
2'5'-dideoxyguanosin-4'-ene,
2'5'-dideoxyuridin-4'-ene,
2'5'-dideoxycytidin-4'-ene,
5'-deoxyuridin-4'-ene,
9-(2,5-dideoxy-β-D-erythro-pent-4-enofuranosyl)2,6-diaminopurine, 1-(2,5-dideoxy-β-D-erythro-pent-4-enofuranosyl)5-trifluoromethyl-2,4-dioxopyrimidine, 9-(2,5-dideoxy-β-D-erythro-pent-4-enofuranosyl)2-aminopurine, 1-(2,5-dideoxy-β-D-erythro-pent-4-enofuranosyl)5-fluoro-2,4-dioxopyrimidine, 1-(2,5-dideoxy-β-D-erythro-pent-4-enofuranosyl)5-chloro-2,4-dioxopyrimidine, 1-(2,5-dideoxy-β-D-erythro-pent-4-enofuranosyl)5-bromo-2,4-dioxopyrimidine, and 1-(2,5-dideoxy-β-D-erythro-pent-4-enofuranosyl)5-iodo-2,4-dioxopyrimidine;

there are obtained the following respective compounds:

4'-azido-2',5'-dideoxy-5'-iodoadenosine,
4'-azido-2',5'-dideoxy-5'-iodoguanosine,
4'-azido-2',5'-dideoxy-5'-iodouridine,
4'-azido-2',5'-dideoxy-5'-iodocytidine,
4'-azido-5'-deoxy-5'-iodouridine,
9-(4-azido-2,5-dideoxy-5-iodo-β-D-erythro-pentofuranosyl)2,6-diaminopurine,
1-(4-azido-2,5-dideoxy-5-iodo-β-D-erythro-pentofuranosyl)5-trifluoromethyl-2,4-dioxopyrimidine,
9-(4-azido-2,5-dideoxy-5-iodo-β-D-erythro-pentofuranosyl)2-aminopurine,
1-(4-azido-2,5-dideoxy-5-iodo-β-D-erythro-pentofuranosyl)5-fluoro-2,4-dioxopyrimidine,
1-(4-azido-2,5-dideoxy-5-iodo-β-D-erythro-pentofuranosyl)5-chloro-2,4-dioxopyrimidine,
1-(4-azido-2,5-dideoxy-5-iodo-β-D-erythro-pentofuranosyl)5-bromo-2,4-dioxopyrimidine, and
1-(4-azido-2,5-dideoxy-5-iodo-β-D-erythro-pentofuranosyl)5-iodo-2,4-dioxopyrimidine.

Preparation 4

4A. Formula 3 Where B is Uridine, X and Y are H, X' is OH

5'-Deoxy-5'-iodouridine (2.018 g; 5.7 mM) was dissolved in 20 mL of dimethylformamide under nitrogen. 1,5-Diazabicyclo[4.3.0]non-5-ene (DBN) (1.6 mL, 12.95 mM) was added dropwise and the resulting mixture was stirred at room temperature for 20 hours. The solvent was evaporated under high vacuum (30° C.) and the evaporation was repeated after the addition of 8 mL of toluene. The oily residue was chromatographed on a silica gel column using 10% methanol/CH$_2$Cl$_2$ (v/v) as eluent. The desired product was isolated as 439 mg of material, which was crystallized from ethyl acetate:hexane to provide crystalline 5'-deoxyuridin-4'-ene (207 mg; 1.36 mM; 24%) (mp 167°–169° C.).

4B. Formula 3 Varying B

By following the procedure of Part A and substituting 5'-deoxy-5'-iodouridine with the following:

1-(5-deoxy-5-iodo-β-D-ribofuranosyl)thymine,
5'-deoxy-5'-iodoadenosine,
5'-deoxy-5'-iodoguanosine,
9-(5-deoxy-5-iodo-β-D-ribofuranosyl)2-aminopurine,
9-(5-deoxy-5-iodo-β-D-ribofuranosyl)2,6-diaminopurine,
9-(5-deoxy-5-iodo-β-D-ribofuranosyl)hypoxanthine, and
1-(5-deoxy-5-iodo-β-D-ribofuranosyl)5-trifluoromethyl-2,4-dioxopyrimidine;

there are obtained the following respective compounds:

1-(5-deoxy-β-D-ribopent-4-enofuranosyl)thymine,
5'-deoxyadenosin-4'-ene,
5'-deoxyguanosin-4'-ene,
9-(5-deoxy-β-D-ribopent-4-enofuranosyl)2-aminopurine,
9-(5-deoxy-β-D-ribopent-4-enofuranosyl)2,6-diaminopurine,
9-(5-deoxy-β-D-ribopent-4-enofuranosyl)hypoxanthine, and
1-(5-deoxy-β-D-ribopent-4-enofuranosyl)5-trifluoromethyl-2,4-dioxopyrimidine.

Preparation 5

5A. Formula 4 Where B is Uridine, X and Y are H, X' is OH

Sodium azide (441 mg, 6.79 mM) was suspended in 5 mL of DMF under nitrogen. A solution of iodine monochloride (550 mg, 3.39 mM) in 2 mL of dimethylformamide was added dropwise. The resulting mixture was stirred at room temperature for 5 min. A solution of 5'-deoxyuridin-4'-ene (307 mg; 1.36 mM) in 20 mL of dimethylformamide was added dropwise with stirring over a period of 20 min. Stirring at room temperature was continued for 1 hour, then 10 mL of saturated sodium bicarbonate followed by 2 mL of sodium thiosulfate in water (10% v/v) was added. The resulting suspension was filtered through celite and the clear filtrate was evaporated under high vacuum at 30° C. to give a semi-solid residue. Chromatography of the residue on silica gel followed by precipitation from ethyl acetate/hexane gave 1-(4-azido-5-deoxy-5-iodo-α-L-lyxofuranosyl)uracil (46 mg) and 4'-azido-5'-deoxy-5'-iodouridine (305 mg) as white powders.

5B. Formula 4 Varying B

By following the procedure of Part A and substituting 5'-deoxyuridin-4'-ene with the following:

1-(5-deoxy-β-D-ribopent-4-enofuranosyl)thymine,
5'-deoxyadenosin-4'-ene,
5'-deoxyguanosin-4'-ene,
9-(5-deoxy-β-D-ribopent-4-enofuranosyl)2-aminopurine,
9-(5-deoxy-β-D-ribopent-4-enofuranosyl)2,6-diaminopurine,
9-(5-deoxy-β-D-ribopent-4-enofuranosyl)hypoxanthine, and
1-(5-deoxy-β-D-ribopent-4-enofuranosyl)5-trifluoromethyl-2,4-dioxopyrimidine;

there are obtained the following respective compounds:

1-(4-azido-5-deoxy-5-iodo-β-D-ribofuranosyl)thymine,
4'-azido-5'-deoxy-5'-iodoadenosine,
4'-azido-5'-deoxy-5'-iodoguanosine,
9-(4-azido-5-deoxy-5-iodo-β-D-ribofuranosyl)2-aminopurine,
9-(4-azido-5-deoxy-5-iodo-β-D-ribofuranosyl)2,6-diaminopurine,
9-(4-azido-5-deoxy-5-iodo-β-D-ribofuranosyl)hypoxanthine, and
1-(4-azido-5-deoxy-5-iodo-β-D-ribofuranosyl)5-trifluoromethyl-2,4-dioxopyrimidine.

Preparation 6

6A. Formula 6 Where B is Thymine; Y' is F; and Y, X and X' are H

3'-Deoxy-3'-fluorothymidine (2.04 g, 8.34 mM) and o-nitrophenylselenocyanate (2.10 g, 9.20 mM) were placed in a flask under nitrogen. Tetrahydrofuran (dry) (50 mL) was added followed by 2.2 mL (8.83 mM) of tri-n-butylphosphine. The mixture was stirred at room temperature for 1.5 hours, diluted with 200 mL of ethyl acetate and washed with 200 mL of sat. sodium bicarbonate followed by 200 mL of brine. The extract was dried over magnesium sulfate and concentrated under reduced pressure to a yellow oil (6.3 g). Chromatographic purification of the yellow oil on silica gel with hexane:ethyl acetate (4:1 v/v) as eluent gave 2.79 g (6.51 mM; 78%) of 3',5'-di-deoxy-3'-fluoro-5'-[(2-nitrophenyl)selenyl]thymidine as an amorphous yellow solid.

6B Formula 6 Varying B

By following the procedure of part A and substituting 3' -deoxy-3 '-fluorothymidine with the following:

2',3'-dideoxy-3'-fluoroadenosine,
2',3'-dideoxy-3'-fluorouridine,
2',3'-dideoxy-3'-fluorocytidine,
2',3'-dideoxy-3'-fluoroguanosine,
9-(2,3-dideoxy-3-fluoro-β-D-erythro-pentofuranosyl)2-aminopurine
9-(2,3-dideoxy-3-fluoro-β-D-erythro-pentofuranosyl)2,6-diaminopurine,
9-(2,3-dideoxy-3-fluoro-β-D-erythro-pentofuranosyl)hypoxanthine, and
1-(2,3-dideoxy-3-fluoro-β-D-erythro-pentofuranosyl)5-trifluoromethyluracil;

there are obtained the following respective compounds:

2',3',5'-trideoxy-3'-fluoro-5'-[(2-nitrophenyl)selenyl]adenosine,
2',3',5'-trideoxy-3'-fluoro-5'-[(2-nitrophenyl)selenyl]uridine,
2',3',5'-trideoxy-3'-fluoro-5'-[(2-nitrophenyl)selenyl]cytidine,
2',3',5'-trideoxy-3'-fluoro-5'-[(2-nitrophenyl)selenyl]guanosine,
9-{2,3,5-trideoxy-3-fluoro-5-[(2-nitrophenyl)selenyl]-β-D-erythro-pentofuranosyl}2-aminopurine
9-{2,3,5-trideoxy-3-fluoro-5-[(2-nitrophenyl)selenyl]β-D-erythro-pentofuranosyl}2,6-diaminopurine,
9-{2,3,5-trideoxy-3-fluoro-5-[(2-nitrophenyl)selenyl]-β-D-erythro-pentofuranosyl}hypoxanthine, and
1-{2,3,5-trideoxy-3-fluoro-5-[(2-nitrophenyl)selenyl]-β-D-erythro-pentofuranosyl}5-trifluoromethyluracil.

Preparation 7

7A. Formula 8 Where B is Thymine; Y' is F; and Y, X and X' are H

3',5'-Dideoxy-3'-fluoro-5'-[(2-nitrophenyl)selenyl]thymidine (2.79 g, 6.51 mM) was dissolved in 53 mL of methylene chloride. Saturated sodium bicarbonate (17.8 mL) was added followed under vigorous stirring by 3-chloroperoxybenzoic acid (85% grade) (1.37 g, 6.83 mM). The mixture was stirred for 1 hour at room temperature, then poured into 200 mL of 10% (w/v) sodium thiosulfate/water. The mixture was extracted twice with 200 mL of 10% n-butanol/chloroform. The extracts were washed with brine, combined and dried over magnesium sulfate. Concentration under reduced pressure gave 2.90 g of selenoxides as a yellow solid.

The crude selenoxides (2.90 g) were suspended in 100 mL of toluene and triethylamine (3.0 mL, 21.5 mM) was added. The mixture was heated to 100° C. for 1 hour, cooled to room temperature and evaporated at reduced pressure to a semi-solid residue. Chromatography of the residue on silica gel with ethyl acetate:hexane (4:1 v/v) as eluent and crystallization from ethyl acetate/hexane gave 650 mg (2.87 mM, 44%) of 3',5'-dideoxy-3'-fluorothymidin-4'-ene (mp 167°–169° C.).

7B Formula 8 Varying B

By following the procedure of part A and substituting 3',5'-dideoxy-3'-fluoro-5'-[(2-nitrophenyl)selenyl]thymidine with the following:

2',3',5'-trideoxy-3'-fluoro-5'-[(2-nitrophenyl)selenyl]adenosine,
2',3',5'-trideoxy-3'-fluoro-5'-[(2-nitrophenyl)selenyl]uridine,
2',3',5'-trideoxy-3'-fluoro-5'-[(2-nitrophenyl)selenyl]cytidine,
2',3',5'-trideoxy-3'-fluoro-5'-[(2-nitrophenyl)selenyl]guanosine,
9-{2,3,5-trideoxy-3-fluoro-5-[(2-nitrophenyl)selenyl]-β-D-erythro-pentofuranosyl}2-aminopurine,
9-{2,3,5-trideoxy-3-fluoro-5-[(2-nitrophenyl)selenyl]-β-D-erythro-pentofuranosyl}2,6-diaminopurine,
9-{2,3,5-trideoxy-3-fluoro-5-[(2-nitrophenyl)selenyl]-β-D-erythro-pentofuranosyl}hypoxanthine, and
1-{2,3,5-trideoxy-3-fluoro-5-[(2-nitrophenyl)selenyl]-β-D-erythro-pentofuranosyl}5-trifluoromethyluracil;

there are obtained the following respective compounds:

2',3',5'-trideoxy-3'-fluoroadenosin-4'-ene,
2',3',5'-trideoxy-3'-fluorouridin-4'-ene
2',3',5'-trideoxy-3'-fluorocytidin-4'-ene,
2',3',5'-trideoxy-3'-fluoroguanosin-4'-ene,
9-(2,3,5-trideoxy-3-fluoro-β-D-erythro-pent-4-enofuranosyl)2-aminopurine,
9-(2,3,5-trideoxy-3-fluoro-β-D-erythro-pent-4-enofuranosyl)2,6-diaminopurine,
9-(2,3,5-trideoxy-3-fluoro-β-D-erythro-pent-4-enofuranosyl)hypoxanthine, and
1-(2,3,5-trideoxy-3-fluoro-β-D-erythro-pent-4-enofuranosyl)5-trifluoromethyluracil.

Preparation 8

8A. Formula 6 Where B is Thymine; and X, X', Y and Y' are H

3'-Deoxythymidine (2.0 g, 8.84 mM) and o-nitrophenylselenocyanate (2.16 g, 9.51 mM) were placed in a flask under nitrogen. Tetrahydrofuran (dry) (50 mL) was added followed by tri-n-butylphosphine (2.4 mL, 9.63 mM). The mixture was stirred at room temperature for 1 hour, diluted with 250 mL of ethyl acetate and washed with 250 mL of sat. sodium bicarbonate followed by 250 mL of brine. The organic phase was dried over magnesium sulfate and concentrated under reduced pressure to a yellow oil (6.3 g). Chromatography of the crude oil on silica gel with a hexane:ethyl acetate (1:10 v/v) gave 2',3',5'-trideoxy-5'-[(2-nitrophenyl)selenyl]thymidine (3.15 g, 7.67 mM, 87%) as an amorphous yellow solid.

8B. Formula 6 Varying B

By following the procedure of part A and substituting 3'-deoxythymidine with the following:

2',3'-dideoxyadenosine,
2',3'-dideoxyuridine,
2',3'-dideoxycytidine,
2',3'-dideoxyguanosine,
9-(2,3-dideoxy-β-D-erythro-pentofuranosyl)2-aminopurine,
9-(2,3-dideoxy-β-D-erythro-pentofuranosyl)2,6-diaminopurine,
9-(2,3-dideoxy-β-D-erythro-pentofuranosyl)hypoxanthine, and
1-(2,3-dideoxy-β-D-erythro-pentofuranosyl)5-trifluoromethyluracil;

there are obtained the following respective compounds:

5'-[(2-nitrophenyl)selenyl]-2',3',5'-trideoxyadenosine
5'-[(2-nitrophenyl)selenyl]-2',3',5'-trideoxyuridine,
5'-[(2-nitrophenyl)selenyl]-2',3',5'-trideoxycytidine,
5'-[(2-nitrophenyl)selenyl]-2',3',5'-trideoxyguanosine, 9-{5-[(2-nitrophenyl)selenyl]-2,3,5-trideoxy-β-D-erythro-pentofuranosyl}2-aminopurine, 9-{5-[(2-nitrophenyl)selenyl]-2,3,5-trideoxy-β-D-erythro-pentofuranosyl }2,6-diaminopurine, 9-{5-[(2-nitrophenyl)selenyl]-2,3,5-trideoxy-β-D-erythro-pentofuranosyl}hypoxanthine, and 1-{5-[(2-nitrophenyl)selenyl]-2,3,5-trideoxy-β-D-erythro-pentofuranosyl}5-trifluoromethyluracil.

Preparation 9

9A. Formulae 8 and 9 Where B is Thymine; and X, X', Y and Y' are H

The 3',5'-dideoxy-5'-[(2-nitrophenyl)selenyl]thymidine (3.04 g, 7.41 mM) was dissolved in 20 mL of methylene chloride. Saturated sodium bicarbonate (20 mL) was added followed under vigorous stirring by 3-chloroperoxybenzoic acid (85% grade) (1.58 g, 7.78 mM). The mixture was stirred for 20 min at room temperature, then poured into 20 mL of 10% (v/v) sodium thiosulfate/water. The mixture was extracted twice with 200 mL of methylene chloride and three times with chloroform (2×200 mL, 1×100 mL). The extracts were washed with brine, combined and dried over magnesium sulfate. Evaporation of the solvent gave 3.06 g of selenoxides as a yellow solid.

The crude selenoxides (3.00 g,) were suspended in 100 mL of toluene and triethylamine (3.0 mL, 21.5 mM) was added. The mixture was refluxed for 1 hour, cooled to room temperature, and evaporated at reduced pressure to a semi-solid residue. Chromatography of the residue on silica gel with ethyl acetate:hexane (6:4 v/v) as eluent, followed by crystallization from ethyl acetate/hexane gave 3',5'-dideoxythymidin-4'-ene 646 mg (44%) (mp 149°–153° C.) and 3',5'-dideoxythymidin-3'-ene (286 mg, 19.5%) (mp 155°–156° C.).

9B. Formula 8 Varying B

By following the procedure of part A and substituting for 3',5'-dideoxy-5'-[(2-nitrophenyl)selenyl]thymidine with the following:

5'-[(2-nitrophenyl)selenyl]-2',3',5'-trideoxyadenosine,
5'-[(2-nitrophenyl)selenyl]-2',3',5'-trideoxyuridine,
5'-[(2-nitrophenyl)selenyl]-2',3',5'-trideoxycytidine,
5'-[(2-nitrophenyl)selenyl]-2',3',5'-trideoxyguanosine,
9-{5-[(2-nitrophenyl)selenyl]-2,3,5-trideoxy-β-D-erythro-pentofuranosyl}2-aminopurine,
9-{5-[(2-nitrophenyl)selenyl]-2,3,5-trideoxy-β-D-erythro-pentofuranosyl}2,6-diaminopurine,
9-{5-[(2-nitrophenyl)selenyl]-2,3,5-trideoxy-β-D-erythro-pentofuranosyl}hypoxanthine, and
1-{5-[(2-nitrophenyl)selenyl]-2,3,5-trideoxy-β-D-erythro-pentofuranosyl}5-trifluoromethyluracil;

there are obtained the following respective compounds:

2',3',5'-trideoxyadenosin-4'-ene,
2',3',5'-trideoxyuridin-4'-ene,
2',3',5'-trideoxycytidin-4'-ene,
2',3',5'-trideoxyguanosin-4'-ene,
9-(2,3,5-trideoxy-β-pent-4-enofuranosyl)2-aminopurine,
9-(2,3,5-trideoxy-β-pent-4-enofuranosyl)2,6-diaminopurine,
9-(2,3,5-trideoxy-β-pent-4-enofuranosyl)hypoxanthine, and
1-(2,3,5-trideoxy-β-pent-4-enofuranosyl)5-trifluoromethyluracil.

Preparation 10

4'-Azido-3',5'-di-0-acetyl-2'-deoxyuridine

To 4'-azido-2'-deoxyuridine (270 mg, 1 mM) and 5 mg of 4-dimethylamino-pyridine in a solution of 5 mL of pyridine is added acetic anhydride (0.5 mL). The mixture is stirred at room temperature for 6 hours, methanol (0.2 mL) is added and the solvent evaporated. The residue is purified by chromatography to give the title compound, 4'-azido-3',5'-di-0-acetyl-2'-deoxyuridine.

EXAMPLE 1

3'-0-p-Anisoyl-4'-azido-5'-deoxy-5'-iodothymidine

1A. Formula II Where J is Thymine, Z is Iodomethyl Z' is Azido, Y' is 0-p-anisoyl, and X, X' and Y are M A solution of 4'-azido-5'-deoxy-5'-iodothymidine (11 g, 28 mM), a compound of Formula 4 prepared, for example, as described in Preparation 3A, and p-anisoyl chloride (5.3 g, 31 mM) in pyridine (100 mL) was kept at 21° C. for 16 hours. Methanol (10 mL) was added and the solution was concentrated by evaporation to a viscous sirup. The sirup was chromatographed on a column of silica-gel (800 g) using 2% methanol in dichloromethane as eluent. Pure 3'-0-p-anisoyl-4'-azido-5'-deoxy-5'-iodothymidine (the title compound) (13 g, 95%) was recovered as a foam which crystallized from ethanol (mp 153°–154°).

1B. Formula II Varying B and X'

By following the procedure of part A and substituting for 4'-azido-5'-deoxy-5'-iodothymidine the following:

4'-azido-2',5'-dideoxy-5'-iodoadenosine,
4'-azido-2',5'-dideoxy-5'-iodoguanosine,
4'-azido-2',5'-dideoxy-5'-iodouridine,
4'-azido-2',5'-dideoxy-5'-iodocytidine,
4'-azido-5'-deoxy-5'-iodouridine.
9-(4-amino-2,5-dideoxy-5-iodo-β-D-erythro-pentofuranosyl)2,6-diaminopurine,
1-(4-azido-2,5-dideoxy-5-iodo-β-D-erythro-pentofuranosyl)5-trifluoromethyl-2,4-dioxopyrimidine,
9-(4-azido-2,5-dideoxy-5-iodo-β-D-erythro-pentofuranosyl)2-aminopurine,
1-(4-azido-2,5-dideoxy-5-iodo-β-D-erythro-pentofuranosyl)5-fluoro-2,4-dioxopyrimidine,
1-(4-azido-2,5-dideoxy-5-iodo-β-D-erythro-pentofuranosyl)5-chloro-2,4- dioxopyrimidine,
1-(4-azido-2,5-dideoxy-5-iodo-β-D-erythro-pentofuranosyl)5-bromo-2,4-dioxopyrimidine, and
1-(4-azido-2,5-dideoxy-5-iodo-β-D-erythro-pentofuranosyl)5-iodo-2,4-dioxopyrimidine;

there are obtained the following respective compounds:
$N^6,O^{3'}$-di-p-anisoyl-4'-azido-2',5'-dideoxy-5'-iodoadenosine,
$N^2,O^{3'}$-di-p-anisoyl-4'-azido-2',5'-dideoxy-5'-iodoguanosine,
3'-0-p-anisoyl-4'-azido-2',5'-dideoxy-5'-iodouridine,
$N^4,O^3$-di-p-anisoyl-4'-azido-2',5'-dideoxy-5'-iodocytidine,
2',3'-di-0-p-anisoyl-4'-azido-5'-deoxy-5'-iodouridine,
$N^2,N^6$-di-p-anisoyl-9-(3-0-p-anisoyl-4-azido-2,5-dideoxy-5-iodo-β-D-erythro-pentofuranosyl)2,6-diaminopurine,
1-(3-0-p-anisoyl-4-azido-2,5-dideoxy-5-iodo-β-D-erythro-pentofuranosyl)5-trifluoromethyl-2,4-dioxopyrimidine, N²-p-anisoyl-9-(3-0-p-anisoyl-4-azido-2,5-dideoxy-5-iodo-β-D-erythro-pentofuranosyl)2-aminopurine, 1-(3-0-p-anisoyl-4-azido-2,5-dideoxy-5-iodo-β-D-erythro-pentofuranosyl)5-fluoro-2,4-dioxopyrimidine, 1-(3-0-p-anisoyl-4-azido-2,5-dideoxy-5-iodo-β-D-erythro-pentofuranosyl)5-chloro-2,4-dioxopyrimidine, 1-(3-0-p-anisoyl-4-azido-2,5-dideoxy-5-iodo-β-D-erythro-pentofuranosyl)5-bromo-2,4-dioxopyrimidine, and 1-(3-0-p-anisoyl-4-azido-2,5-dideoxy-5-iodo-β-D-erythro-pentofuranosyl)5-iodo-2,4-dioxopyrimidine.

1C. Formula II Where Y' is 0-benzoyl

By following the procedure of part A and substituting for p-anisoyl chloride an equivalent amount of benzoyl chloride, there is obtained 4'-azido-3'-0-benzoyl-5'-deoxy-5'-iodothymidine.

EXAMPLE 2

4'-Azido-5'-deoxy-2',3'-di-0-benzoyl-5'-iodouridine

2A. Formula II Where B is Uridine, X and Y are H, X" is —OR, and R is Benzoyl

4'-Azido-5'-deoxy-5'-iodouridine (280 mg, 0.71 mM) was dissolved in 3 mL of pyridine. Benzoylchloride (0.25 mL) followed by one crystal of 4-dimethylaminopyridine was added and the resulting mixture was stirred at room temperature for 18 hours. The mixture was cooled in an ice/water bath and 10 drops of methanol was added. The mixture was stirred for 5 min before it was diluted with 50 mL of ethyl acetate and sequentially washed with 50 mL of saturated sodium bicarbonate and 50 mL of brine. The organic extract was dried over magnesium sulfate and evaporated. The resulting yellow oil (437 mg) was chromatographed on silica gel and the product crystallized from ethyl acetate/hexane affording 4'-Azido-5'-deoxy-2',3'-di-0-benzoyl-5'-iodouridine (192 mg, 0.32 mM, mp 120°–122° C.).

2B. Formula II Varying B

By following the procedure of Part A and substituting 4'-azido-5'-deoxy-5'-iodouridine with the following:

1-(4-azido-5-deoxy-5-iodo-β-D-ribofuranosyl)thymine,

4'-azido-5'-deoxy-5'-iodoadenosine,

4'-azido-5'-deoxy-5'-iodoguanosine, 9-(4-azido-5-deoxy-5-iodo-β-D-ribofuranosyl)2-aminopurine, 9-(4-azido-5-deoxy-5-iodo-β-D-ribofuranosyl)2,6-diaminopurine, 9-(4-azido-5-deoxy-5-iodo-β-D-ribofuranosyl)hypoxanthine, and 1-(4-azido-5-deoxy-5-iodo-β-D-ribofuranosyl)5-trifluoromethyl-2,4-dioxopyrimidine;

there are obtained the following respective compounds:

1-(4-azido-5-deoxy-2,3-di-0-benzoyl-5-iodo-β-D-ribofuranosyl)thymine,

N⁶-benzoyl-4'-azido-5'-deoxy-2',3'-di-0-benzoyl-5'-iodoadenosine,

N²-benzoyl-4'-azido-5'-deoxy-2,3-di-0-benzoyl-5'-iodoguanosine,

N²-benzoyl-9-(4-azido-5-deoxy-2,3-di-0-benzoyl-5-iodo-β-D-ribofuranosyl)2-aminopurine, N²,N⁶-dibenzoyl-9-(4-azido-5-deoxy-2,3-di-0-benzoyl-5-iodo-β-D-ribofuranosyl)2,6-diaminopurine, 9-(4-azido-5-deoxy-2,3-di-0-benzoyl-5-iodo-β-D-ribofuranosyl)hypoxanthine, and 1-(4-azido-5-deoxy-2,3-di-0-benzoyl-5-iodo-β-D-ribofuranosyl)5-trifluoromethyluracil.

EXAMPLE 3

4'-Azidothymidine

3A. Formula I Where B is Thymine, n is Zero, Y' is Hydroxyl, X, X' and Y are Hydrogen, and Z' is Azido A solution of 3-chloroperoxybenzoic acid (85% grade, 21.0 g, 103 mM) in dichloromethane saturated with H₂O (150 mL) was added to a stirred solution of 3'-0-p-anisoyl-4'-azido-5'-deoxy-5'-iodothymidine (12.0 g, 22.8 mM), prepared, e.g., as described in Example 1, in dichloromethane saturated with H₂O (150 mL). After 3 hours at 21° C., the reaction mixture was diluted with dichloromethane (200 mL) and n-butanol (50 mL), and then extracted successively with saturated aqueous sodium bisulfite (100 mL), saturated aqueous sodium bicarbonate (100 mL), and H₂O (100 mL). The organic phase was then concentrated in vacuo to a viscous sirup. A solution of the sirup in methanol (250 mL) and concentrated ammonium hydroxide (250 mL) was kept at 21° C. for 16 hours and then the solvent was removed by evaporation. The residue was chromatographed on a column of silica-gel (500 g) and eluted with 8% methanol in dichloromethane. Pure product was recovered and crystallized from ethanol to give the title compound, 4'-azidothymidine (1.46 g, 23%) (mp 175°–176°).

3B. Formula I Varying B and X'

By following the procedure of part A and substituting for 3'-0-p-anisoyl-4'-azido-5'-deoxy-5'-iodothymidine the following:

N⁶,0³'-di-p-anisoyl-4'-azido-2',5'-dideoxy-5'-iodoadenosine,

N²,0³'-di-p-anisoyl-4'-azido-2',5'-dideoxy-5'-iodoguanosine,

3'-0-p-anisoyl-4'-azido-2',5'-dideoxy-5'-iodouridine,

N⁴,0³-di-p-anisoyl-4'-azido-2',5'-dideoxy-5'-iodocytidine,

2',3'-di-O-p-anisoyl-4'-azido-5'-deoxy-5'-iodouridine,

N²,N⁶-di-p-anisoyl-9-(3-O-p-anisoyl-4-azido-2,5-dideoxy-5-iodo-β-D-erythro-pentofuranosyl)2,6-diaminopurine, 1-(3-0-p-anisoyl-4-azido-2,5-dideoxy-5-iodo-β-D-erythro-pentofuranosyl)5-trifluoromethyl-2,4-dioxopyrimidine, N²-p-anisoyl-9-(3-O-p-anisoyl-4-azido-2,5-dideoxy-5-iodo-β-D-erythro-pentofuranosyl)2-aminopurine, 1-(3-0-p-anisoyl-4-azido-2,5-dideoxy-5-iodo-β-D-erythro-pentofuranosyl)5-fluoro-2,4-dioxopyrimidine, 1-(3-0-p-anisoyl-4-azido-2,5-dideoxy-5-iodo-β-D-erythro-pentofuranosyl)5-chloro-2,4-dioxopyrimidine, 1-(3-0-p-anisoyl-4-azido-2,5-dideoxy-5-iodo-β-D-erythro-pentofuranosyl)5-bromo-2,4-dioxopyrimidine, and 1-(3-0-p-anisoyl-4-azido-2,5-dideoxy-5-iodo-β-D-erythro-pentofuranosyl)5-iodo-2,4-dioxopyrimidine;

there are obtained the following respective compounds:

4'-azido-2'-deoxyadenosine (mp 92°–105° C.),

4'-azido-2'-deoxyguanosine (mp 250° C., w/decomposition),

4'-azido-2'-deoxyuridine (mp 272°–273° C.),

4'-azido-2'-deoxycytidine,

4'-azidouridine (mp 86°–93° C.), 9-(4-azido-2-deoxy-β-D-erythro-pentofuranosyl)2,6-diaminopurine, 1-(4-azido-2-deoxy-β-D-erythro-pentofuranosyl)5-trifluoromethyl-2,4-dioxopyrimidine, 9-(4-azido-2-deoxy-β-D-erythro-pentofuranosyl)2-aminopurine, 1-(4-azido-2-deoxy-β-D-erythro-pentofuranosyl)5-fluoro-2,4-dioxopyrimidine, 1-(4-azido-2-deoxy-β-D-erythro-pentofuranosyl)5-chloro-2,4-dioxopyrimidine, 1-(4-azido-2-deoxy-β-D-erythro-pentofuranosyl)5-bromo-2,4-dioxopyrimidine, and 1-(4-azido-2-deoxy-β-D-erythro-pentofuranosyl)5-iodo-2,4-dioxopyrimidine.

3C. Formula I Made From Formula II Where Y' is 0-benzoyl

By following the procedure of part A and substituting for 3'-0-p-anisoyl-4'-azido-5'-deoxy-5 '-iodothymidine an equivalent amount of 4'-azido-3'-0-benzoyl-5'-deoxy-5'-iodothymidine, there is obtained 4'-azidothymidine.

3D. Formula I Varying X, X', Y and Y'

Similarly, by following the procedures of Preparations 1, 2 and 3, and Examples 1 and 2, and substituting for the starting materials in Preparation 1 the corresponding arabinofuranosyl, xylofuranosyl and lyxofuranosyl nucleosides, there are obtained, respectively, the corresponding compounds of Formula I where X is OH, X' is H, Y is H and Y' is OH; where X is H, X' is OH, Y is OH and Y' is H; and where X is OH, X' is H, Y is OH and Y' is H; or the corresponding 2' or 3' deoxy or 2',3'-dideoxy analogs, depending upon the starting material chosen.

EXAMPLE 4

4'-Azidouridine

4A. Formula I Where B is Uridine, X and Y are H, X' and Y' are OH

To a solution of 4'-azido-5'-deoxy-2',3'-di-0-benzoyl-5'-iodouridine (105 mg, 0.17 mM) in 15 mL of methylene chloride (saturated with water) was added 3-chloroperoxybenzoic acid (85% grade) (160 mg, 0.79 mM). The mixture was refluxed for 5 hours, cooled to room temperature, diluted with 100 mL of ethyl acetate and washed sequentially with 80 mL of saturated sodium bicarbonate and 80 mL of brine. The organic extract was dried over magnesium sulfate and concentrated under reduced pressure to yield 122 mg of an oil. This material was dissolved in 2 mL of methanol and treated with 2.5 mL of saturated ammonium hydroxide. The resulting mixture was stirred at room temperature for 1.5 hours, evaporated under reduced pressure and chromatographed on silica gel to give 39 mg of 4'-azidouridine as an amorphous white powder, m.p. 86°-93° C. Accurate Mass calcd. for $C_9H_{10}N_3O_6$ (M—$N_2H$)+: 256.0569. Found: 256.0570.

4B. Formula I Varying B

By following the procedure of Part A and substituting 4'-azido-5'-deoxy-2',3'-di-0-benzoyl-5'-iodouridine with the following:

1-(4-azido-5-deoxy-2,3-di-0-benzoyl-5-iodo-β-D-ribofuranosyl)thymine, $N^6$-benzoyl-4'-azido-5'-deoxy-2',3'-di-0-benzoyl-5'-iodoadenosine, $N^2$-benzoyl-4'-azido-5'-deoxy-2,3-di-0-benzoyl-5'-iodoguanosine, $N^2$-benzoyl-9-(4-azido-5-deoxy-2,3-di-0-benzoyl-5-iodo-β-D-ribofuranosyl)2-aminopurine, $N^2,N^6$-dibenzoyl-9-(4-azido-5-deoxy-2,3-di-0-benzoyl-5-iodo-β-D-ribofuranosyl)2,6-diaminopurine, 9-(4-azido-5-deoxy-2,3-di-0-benzoyl-5-iodo-β-D-ribofuranosyl)hypoxanthine, and 1-(4-azido-5-deoxy-2,3-di-0-benzoyl-5-iodo-β-D-ribofuranosyl)5-trifluoromethyluracil;

there are obtained the following respective compounds:

1-(4-azido-β-D-ribofuranosyl)thymine,

4'-azidoadenosine,

4'-azidoguanosine, 9-(4-azido-β-D-ribofuranosyl)2-aminopurine, 9-(4-azido-β-D-ribofuranosyl)2,6-diaminopurine, 9-(4-azido-β-D-ribofuranosyl)hypoxanthine, and 1-(4-azido-β-D-ribofuranosyl)5-trifluoromethyl-2,4-dioxopyrimidine.

EXAMPLE 5

3'-Deoxy-3'-fluoro-4'-methoxythymidine

5A. Formula I Where B is Thymine; Z' is Methoxy Y' is F; and Y, X and X' are H

3',5'-Dideoxy-3'-fluorothymidin-4'-ene (400 mg, 1.77 mM) was dissolved in 40 mL of methanol under nitrogen. Solid sodium bicarbonate (178 mg, 2.44 mM) was added followed by 3-chloroperoxybenzoic acid (496 mg, 2.44 mM). The mixture was stirred at room temperature for 5 hours and 3-chloroperoxybenzoic acid (200 mg, 0.98 mM) and sodium bicarbonate (79 mg, 1.8 mM) were added. After an additional 4 hours, more 3-chloroperoxybenzoic acid (200 mg) and sodium bicarbonate (79 mg) were added. Five hours later, the mixture was diluted with 170 mL of methylene chloride and washed with 170 mL of saturated sodium bicarbonate. The aqueous phase was back extracted once with 170 mL of methylene chloride and twice with 200 mL of ethyl acetate. The organic extracts were combined, dried over magnesium sulfate and concentrated under reduced pressure providing 320 mg of crude product. Chromatography of the crude product on silica gel using 10% methanol/methylene chloride (v/v) as eluent gave 3'-deoxy-3'-fluoro-4'-methoxythymidine as an oil (124 mg, 0.45 mM, 25%). Accurate mass calcd. for $C_{11}H_{15}FN_2O_5$: 274.0965. Found: 274.0961.

5B. Formula I Varying B

By following the procedure of part A and substituting for 3',5'-dideoxy-3'-fluoro-thymidin-4'-ene with the following:

2',3',5'-trideoxy-3'-fluoro-5'-[(2-nitrophenyl)selenyl]adenosine,

2',3',5'-trideoxy-3'-fluoro-5'-[(2-nitrophenyl)selenyl]uridine,

2',3',5'-trideoxy-3'-fluoro-5'-[(2-nitrophenyl)selenyl]cytidine,

2',3',5'-trideoxy-3'-fluoro-5'-[(2-nitrophenyl)selenyl]guanosine,

9-{2,3,5-trideoxy-3-fluoro-5-[(2-nitrophenyl)selenyl]-β-D-erythro-pentofuranosyl}2-aminopurine, 9-{2,3,5-trideoxy-3-fluoro-5-[(2-nitrophenyl)selenyl]-β-D-erythro-pentofuranosyl}2,6-diaminopurine, 9-{2,3,5-trideoxy-3-fluoro-5-[(2-nitrophenyl)selenyl]-β-D-erythro-pentofuranosyl}hypoxanthine, and 1-{2,3,5-trideoxy-3-fluoro-5-[(2-nitrophenyl)-selenyl]β-D-erythro-pentofuranosyl}5-trifluoromethyluracil;

there are obtained the following respective compounds:

2',3'-dideoxy-3'-fluoro-4'-methoxyadenosine,

2',3'-dideoxy-3'-fluoro-4'-methoxyuridine,

2',3'-dideoxy-3'-fluoro-4'-methoxycytidine,

2',3'-dideoxy-3'-fluoro-4'-methoxyguanosine, 9-(2,3-dideoxy-3-fluoro-4-methoxy-β-D-erythro-pentofuranosyl)2-aminopurine, 9-(2,3-dideoxy-3-fluoro-4-methoxy-β-D-erythro-pentofuranosyl)2,6-diaminopurine, 9-(2,3-dideoxy-3-fluoro-4-methoxy-β-D-erythro-pentofuranosyl)hypoxanthine, and 1-(2,3-dideoxy-3-fluoro-4-methoxy-β-D-erythro-pentofuranosyl)5-trifluoromethyl-2,4-dioxopyrimidine.

EXAMPLE 6

1-(3-Deoxy-4-methoxy-a-L-glycero-pentofuranosyl)thymine

6A. Formula I-B Where $R^3$ is $CH_3$; B is Thymine; and X, X', Y, Y' are H

3',5'-Dideoxythymidin-4'-ene (30 mg, 0.144 mM) was dissolved in 1.0 mL of methanol and kept under nitrogen. Solid potassium bicarbonate (36 mg, 0.36 mM) was added and the mixture was cooled in an ice/water bath. 3-Chloroperoxybenzoic acid (0.214 mM) was added in one lot and the mixture stirred for 3 min. before the reaction was quenched by the addition of 2.0 mL of a 1:1 mixture of saturated sodium bicarbonate and 10% (w/v) sodium thiosulfate in water. The resulting mixture was extracted twice with 50 mL of ethyl acetate:-chloroform (1:3 v/v). The extracts were washed with 2.0 mL of brine, combined, dried over magnesium sulfate and concentrated in vacuo. The residue (31 mg) was chromatographed on two silica gel plates giving 1-(3-deoxy-4-methoxy-α-L-glycero-pentofuranosyl)thymine (8 mg, 31 μM, 22%) as an oil.

6B. Formula I-B Varying B

By following the procedure of part A and substituting 3',5'-dideoxythymidin-4'-ene with the following:

2',3',5'-trideoxyadenosin-4'-ene,
2',3',5'-trideoxyuridin-4'-ene,
2',3',5'-trideoxycytidin-4'-ene,
2',3',5'-trideoxyguanosin-4'-ene,
9-(2,3,5-trideoxy-β-pent-4-enofuranosyl)2-aminopurine,
9-(2,3,5-trideoxy-β-pent-4-enofuranosyl)2,6-diaminopurine,
9-(2,3,5-trideoxy-β-pent-4-enofuranosyl)hypoxanthine, and
1-(2,3,5-trideoxy-β-pent-4-enofuranosyl)5-trifluoromethyluracil;

there are obtained the following respective compounds:

9-(2,3-dideoxy-4-methoxy-α-L-glyceropentofuranosyl)adenine,
1-(2,3-dideoxy-4-methoxy-α-L-glyceropentofuranosyl)uracil,
1-(2,3-dideoxy-4-methoxy-α-L-glyceropentofuranosyl)cytosine,
9-(2,3-dideoxy-4-methoxy-α-L-glyceropentofuranosyl)guanine,
9-(2,3-dideoxy-4-methoxy-α-L-glyceropentofuranosyl)2-aminopurine,
9-(2,3-dideoxy-4-methoxy-α-L-glyceropentofuranosyl)2,6-diaminopurine,
9-(2,3-dideoxy-4-methoxy-α-L-glyceropentofuranosyl)hypoxanthine, and
1-(2,3-dideoxy-4-methoxy-α-L-glyceropentofuranosyl)5-trifluoromethyluracil.

EXAMPLE 7

4'-Azido-3'-deoxythymidine

7A. Formula I Where B is Thymine; X, X', Y and Y' are H; Z' is Azido; and n is Zero 1-(2,3-dideoxy-4-methoxy-α-L-glycero-pentofuranosyl)thymine (19 mg, 74 μM) was dissolved in 2 mL of dimethylformamide under nitrogen and 31 mg (0.45 mM) of imidazole and 31 mg (0.21 mM) of t-butyldimethylsilyl chloride were added. The mixture was stirred at room temperature for 3 hours before the reaction was quenched by the addition of 2 drops of methanol. The mixture was poured into 30 mL of saturated sodium bicarbonate and extracted twice with 50 mL of ethyl acetate. The extracts were washed with brine, dried over magnesium sulfate and concentrated in vacuo. The oily residue (40 mg) was chromatographed on a silica gel plate using chloroform containing 4% of methanol as the eluent. Isolation of the product band gave a silyl ether, 1-[2,3-dideoxy-5-0-(1,1-dimethylethyl)-dimethylsilyl-4-methoxy-α-L-glycero-pentofuranosyl]thymine (24 mg, 65 μm, 89%) as an oil.

The next step was carried out in two batches; 16 mg and 7 mg of silyl ether respectively. The two were combined for workup and purification. The procedure for the larger batch is described below.

The silyl ether (16 mg, 43 μM) was dissolved in 1.5 mL of methylene chloride and azidotrimethylsilane (45 μL) and trimethylsilyl trifluoromethanesulfonate (6 μL) were added.

The mixture was stirred for 72 hours at room temperature and combined with the reaction mixture from the 7 mg batch. Dilution with 50 mL of ethyl acetate: chloroform (1:3 v/v) and washing with 5 mL of saturated sodium bicarbonate followed by 5 mL of brine and drying over magnesium sulfate and subsequent evaporation gave 16 mg of an oil. Chromatography of the oil on silica gel plates followed by crystallization from ethyl acetate: hexane gave 4'-azido-3'-deoxythymidine (5 mg, mp 55°–60° C. decomp.) and 1-(4-azido-2,3-dideoxy-α-L-glycero-pentofuranosyl)thymine (3 mg, mp 129°–131° C.).

7B. Formula I-B varying B

By following the procedure of part A and substituting 1-(2,3-dideoxy-4-methoxy-α-L-glycero-pentofuranosyl)thymine with the following:

9-(2,3-dideoxy-4-methoxy-α-L-glyceropentofuranosyl)adenine,
1-(2,3-dideoxy-4-methoxy-α-L-glyceropentofuranosyl)uracil,
1-(2,3-dideoxy-4-methoxy-α-L-glyceropentofuranosyl)cytosine,
9-(2,3-dideoxy-4-methoxy-α-L-glyceropentofuranosyl)guanine,
9-(2,3-dideoxy-4-methoxy-α-L-glyceropentofuranosyl)2-aminopurine,
9-(2,3-dideoxy-4-methoxy-α-L-glyceropentofuranosyl)2,6-diaminopurine,
9-(2,3-dideoxy-4-methoxy-α-L-glyceropentofuranosyl)hypoxanthine, and
1-(2,3-dideoxy-4-methoxy-α-L-glyceropentofuranosyl)5-trifluoromethyluracil;

there are obtained the following respective compounds:

4'-azido-2',3'-dideoxyadenosine,
4'-azido-2',3'-dideoxyuridine,
4'-azido-2',3'-dideoxycytidine,
4'-azido-2',3'-dideoxyguanosine,
9-(4-azido-2,3-dideoxy-β-D-glyceropentofuranosyl)2-aminopurine,
9-(4-azido-2,3-dideoxy-β-D-glyceropentofuranosyl)2,6-diaminopurine,
9-(4-azido-2,3-dideoxy-β-D-glyceropentofuranosyl)hypoxanthine, and
1-(4-azido-2,3-dideoxy-β-D-glyceropentofuranosyl)5-trifluoromethyl-2,4-dioxopyrimidine.

EXAMPLE 8

4'-Azidothymidine 5'-Monophosphate Disodium Salt

To a suspension of 4'-azidothymidine (0.20 g, 0.71 mM) in ethyl acetate (12 mL) cooled to 0° C. was added pyrophosphoryl chloride (0.5 mL, 3.7 mM). After stirring for 4 hours at 0° C., the solution was neutralized (pH 6 to 7) by the addition of saturated aqueous sodium bicarbonate. The organic phase was discarded, and the aqueous phase was stirred for 20 minutes with activated, 14–60 mesh, charcoal. The charcoal mixture was filtered and the charcoal rinsed with water (200 mL). All filtrates and rinsings were discarded. The charcoal was next washed with 50% aqueous ethanol containing 5% ammonium hydroxide (250 mL). These washings were concentrated in vacuo to about 5 mL and applied onto a 3×23 cm column of DEAE Sephadex (carbonate form). The column was eluted with a linear gradient consisting of 1 L of water and 1 L of 0.5M triethylammonium bicarbonate (pH 7). Pure product was collected and the solvent removed by evaporation. The residue was co-evaporated repeatedly with water, then dissolved in methanol (0.5 mL). The addition of 0.45M sodium perchlorate in acetone (2 mL) to this solution caused the title compound to precipitate out. Filtering off the solid and drying under vacuum left 55 mg of 4'-azidothymidine 5'-monophosphate disodium salt (mp 185° C., decomposition).

EXAMPLE 9

4'-Azidothymidine 5'-Diphosphate Trisodium Salt and 4'-Azidothymine 5'-Triphosphate Tetrasodium Salt A solution of the compound of 4'-azidothymidine 5'-monophosphate disodium salt (55 mg, 0.14 mM) in $H_2O$ (5 mL) is applied onto a short column of Dowex 50 (H+) resin (8 mL) and eluted with $H_2O$. After concentrating the eluent to 5 mL, tributylamine (32 μL) and pyridine (5 mL) was added and the mixture evaporated in vacuo. The residue was co-evaporated with pyridine then with dimethylformamide. To a solution of the residue in dimethylformamide (1 mL) was added a solution of carbonyldiimidazole (0.11 g, 0.66 mM) in dimethylformamide (1.5 mL). After 20 hours at room temperature, methanol (0.04 mL, 1.0 mM) was added. Thirty minutes later a solution of tributylammonium pyrophosphate (0.675 mM) in dimethylformamide (7 mL) was added and mixture was vigorously stirred for 20 hours at room temperature. After filtration, the solution was diluted with an equal volume of methanol and evaporated to a sirup. The sirup was dissolved in water (10 mL) and applied onto a 3×23 cm column of DEAE Sephadex (carbonate form) which was eluted with a linear gradient consisting of 2 L of water and 2 L of 0.5M triethylammonium bicarbonate (pH 7). The 4'-azidothymidine 5'-diphosphate was eluted pure followed by the 4'-azidothymidine 5-'triphosphate. After evaporation of solvent and repeated co-evaporation with water, each product was dissolved in a small amount of methanol. The addition of a 0.45M solution of sodium perchlorate in acetone then precipitated the sodium salts. Filtering off the precipitates and drying in vacuo gave 4'-azidothymidine 5'-diphosphate trisodium salt (12 mg) and 4'-azidothymidine 5'-triphosphate tetrasodium salt (54 mg, mp 204° C., decomposition).

EXAMPLE 10

4'-Azidothymidine 3',5'-Cyclic Phosphate Sodium Salt

4'-Azidothymidine 5'-monophosphate disodium salt, prepared, e.g., as described in Example 8, is passed through a column of Dowex 50-X8 cation-exchange resin (H+ form) with water as eluent. Upon evaporation of the water, the residue is dissolved in a mixture of pyridine and water containing N,N'-di-cyclohexyl-4-morpholinecarboxamidine, and is then evaporated in vacuo. The residue is co-evaporated three times with pyridine. A solution of the resulting sirup in pyridine is added dropwise over 1 hour to a refluxing solution of dicyclohexylcarbodiimidate in pyridine. When the addition is complete, the mixture is heated at reflux for an additional 2.5 hours, followed by removal of the solvent by evaporation in vacuo. A solution of the residue in water is extracted with 10% butanol in dichloromethane, and then with diethyl ether. The aqueous solution is concentrated by evaporation and applied onto a 3×23 cm column of DEAE Sephadex (carbonate form) which is eluted with a linear gradient consisting of 1 L of water and 1 L of 0.5M triethylammonium bicarbonate (pH 7). Eluent containing the pure product is evaporated in vacuo, and the residue co-evaporated repeatedly with water. To a concentrated solution of the residue in methanol is added a 0.45M solution of sodium perchlorate in acetone. The precipitated product is removed and dried to give the title compound 4'-azidothymidine 3',5'-cyclic phosphate sodium salt.

In a similar manner, the other compounds of Formula I where n is 1 can be converted to the cyclic phosphate form. By substituting calcium chloride for sodium perchlorate, the 4'-azidothymidine 3',5'-cyclic phosphate calcium salt is obtained.

EXAMPLE 11

Sodium Salt of 4'-Azidothymidine

4'-Azidothymidine is dissolved in water. One molar equivalent of sodium hydroxide in water is added and the solution is stirred for 1 hour. The solution is then lyophilized to isolate the sodium salt of 4'-azidothymidine.

In a similar manner, all compounds of Formula I where n is zero may be converted to the base addition salts by treatment with the appropriate base, for example, sodium hydroxide, potassium hydroxide, lithium hydroxide, and the like.

EXAMPLE 12

3',5'-Di-adamantoyl Ester of 4'-Azidothymidine

4'-Azidothymidine (280 mg) and 10 mg of 4-dimethylaminopyridine in a solution of 7 ml of pyridine is added 2.1 equivalents of adamantanecarboxylic acid chloride as a solution in 3 ml of methylene chloride. The solution is magnetically stirred for 18 hours at 21° C. and 1 ml of methanol is then added. The solution is concentrated and the residue is purified by chromatography to give the title compound, 4'-azidothymidine 3',5'-diadamantoate.

Similarly, by substituting for adamantanecarboxylic acid chloride two molar equivalents of palmitic acid chloride, there is obtained 4'-azidothymidine 3',5'-dipalmitoate.

EXAMPLE 13

4'-Azido-3',5'-di-0-(1,4-dihydro-1-methyl-3-pyridinyl-carbonyl)thymidine

4'-Azidothymidine (3.11 g, 11 mM) is dissolved in dry pyridine (20 mL), then the pyridine is removed in vacuo; this is repeated three times. Finally, 4'-azidothymidine is dissolved in pyridine (20 mL) and nicotinyl chloride (4.68 g, 26 mM) is added. The mixture is maintained at 70° C. for 1.5 hours. The reaction is cooled and the pyridine removed under vacuo. the residue is purified by chromatography. The appropriate fractions are combined to give, after evaporation of the eluent, the title compound, 4'-azido-3',5'-di-0-(1,4-dihydro-1-methyl-3-pyridinylcarbonyl)thymidine, which is then triturated with hexane.

EXAMPLE 14

4'-Azido-3',5'-di-0-isopropylthymidine

4'-Azido-N$^3$benzoylthymidine (1 mM) prepared according to the method of M. Sekine et al., *Synthesis* 1119 (1987), is dissolved in dimethylsulfoxide (10 mL) and sodium hydride (2.1 equivalents) is added, and the mixture is stirred at room temperature for 30 minutes. to this mixture, 2-iodopropane (10 equivalents) is added and the mixture is left at 60° C. until most of the starting material has disappeared, as monitored by thin layer chromatography. The reaction mixture is partitioned between brine and ethyl acetate. The organic phase is dried and evaporated to dryness. The residue is dissolved in saturated methanolic ammonia and left for 1 hour at room temperature. The solvent is evaporated to dryness and the residue is purified by column chromatography to give the title compound, 4'-azido-3',5'-di-0-isopropylthymidine.

EXAMPLE 15

This example illustrates the preparation of a representative pharmaceutical formulation for oral administration containing an active compound of Formula I, e.g., 1-(4-azido-2-deoxy-β-D-erythropentofuranosyl)5-bromo-2,4-dioxopyrimidine.

| Ingredients | Quantity per tablet, mgs. |
| --- | --- |
| Active compound | 200 |
| lactose, spray-dried | 148 |
| magnesium stearate | 2 |

The above ingredients are mixed and introduced into a hard-shell gelatin capsule.

Other compounds of Formula I, such as those prepared in accordance with Examples 3-14, such as 3'-fluoro-4'-methoxythymidine, can be used as the active compound in the preparation of the orally administrable formulations of this example.

EXAMPLE 16

This example illustrates the preparation of a representative pharmaceutical formulation containing an active compound of Formula I, e.g., 4'-azidothymidine.

An suspension for oral administration is prepared having the following composition:

| Ingredients | Quantity |
| --- | --- |
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Other compounds of Formula I, such as those prepared in accordance with Examples 3-14, such as 3'-fluoro-4'-methoxythymidine, can be used as the active compound in the preparation of the orally administrable formulations of this example.

EXAMPLE 17

This example illustrates the preparation of a representative pharmaceutical formulation containing an active compound of Formula I, e.g., 4'-azidothymidine.

An injectable preparation is prepared having the following composition:

| Ingredients | |
| --- | --- |
| Active compound | 0.2 g |
| water (distilled, sterile) | q.s. to 20.0 mL |

Other compounds of Formula I, such as those prepared in accordance with Examples 3-14, such as 3'-fluoro-4'-methoxythymidine, can be used as the active compound in the preparation of the injectable formulations of this example.

Compounds of Formula I having low solubility in water can be formulated for intravenous injection in liposomes.

EXAMPLE 18

This example illustrates the preparation of a representative pharmaceutical formulation for topical application containing an active compound of Formula I, e.g., 1-(4-azido-2-deoxy-β-D-erythro-pentofuranosyl) 5-chloro-2,4-dioxopyrimidine.

| Ingredients | grams |
| --- | --- |
| Active compound | 0.2-10 |
| Span 60 | 2.0 |
| Tween 60 | 2.0 |
| Mineral oil | 5.0 |
| Petrolatum | 10.0 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added, q.s. to 100 g.

Other compounds of Formula I, such as those prepared in accordance with Examples 3-14, such as 3'-fluoro-4'-methoxythymidine can be used as the active compound in the preparation of the topical formulations of this example.

EXAMPLE 19

This example illustrates the preparation of a representative pharmaceutical formulation containing an active compound of Formula I, e.g., 4'-azidothymidine.

A suppository totalling 2.5 grams is prepared having the following composition:

| | |
|---|---|
| Active compound | 500 mg |
| witepsol H-15* | balance |

(*triglycerides of saturated vegetable fatty acid; a product of Riches-Nelson, Inc., New York, N.Y.).

Other compounds of Formula I, such as those prepared in accordance with Examples 3–14, such as 3'-fluoro-4'-methoxythymidine can be used as the active compound in the preparation of the suppository formulations of this example.

EXAMPLE 20

This example illustrates the preparation of another representative pharmaceutical formulation for oral administration, containing an active compound of Formula I, e.g., 4'-azidothymidine.

| Ingredients | Quantity per tablet, mgs. |
|---|---|
| Active compound | 400 |
| cornstarch | 50 |
| lactose | 145 |
| magnesium stearate | 5 |

The above ingredients are mixed intimately and pressed into single scored tablets.

Other compounds of Formula I, such as those prepared in accordance with Examples 3–14, such as 3'-fluoro-4'-methoxythymidine can be used as the active compound in the preparation of the orally administrable formulations of this example.

EXAMPLE 21

Liposome Formulation With 4'-Azidothymidine 5'-monophosphate

Sufficient water is added to 100 g of egg-yolk phospholipids to bring the total volume to 1 liter. The mixture is stirred with a homomixer. Then, the mixture is homogenized with an emulsifier under a pressure of 300 kg/cm$^2$ for 30 minutes, whereby an aqueous phospholipid dispersion is obtained. 4'-Azidothymidine 5'-monophosphate (20 g) and sodium chloride (18 g) are dissolved in enough water to bring the total volume to 1 liter. The aqueous phospholipid dispersion (850 mL) and the 4'-azidothymidine 5'-monophosphate solution (850 mL) are mixed. The aqueous dispersion thus obtained is filtered through a membrane filter (pore size: 0.45$\mu$ in diameter). The filtrate is sterilized at 120° C. for 20 minutes and then allowed to stand at $-20°$ C. for 20 hours in a freezer. The frozen dispersion thus obtained is thawed by allowing it to stand at room temperature. An aqueous suspension of 4'-azidothymidine 5'-monophosphate entrapped in phospholipid spherules is thereby obtained.

Other compounds of Formula I, such as those prepared in accordance with Examples 3–14, particularly the phosphate esters, can be used as the active compound in the preparation of formulation according to this example.

EXAMPLE 22

Liposome Formulation With 4'-Azidothymidine 2',3'-dipalmitoate

Phosphatidylcholine (30 $\mu$M), cholesterol (15 $\mu$M) and cholesterol sulfate (5$\mu$M) are dissolved in a 2:1 mixture of chloroform:methanol. To this, 4'-azidothymidine 3',5'-dipalmitoate (5 $\mu$M) is added and the mixture is stirred in a round bottom flask. The solvents are removed by evaporation under reduced pressure to form a film on the inner surface of the flask. The film is dried in vacuo. Saline (2.5 mL) is added and the solution is shaken under N$_2$ to swell the film and prepare a lipid suspension. The suspension is sonicated at 10°–17° C. for 50 minutes at 20 KHz and 35 W by a probe-type sonicator under N$_2$. The size of the liposomes obtained range from 22–55 mm in diameter.

Other compounds of Formula I, such as the 3',5'-diadamantoate, preferably the long chain acyl derivatives of Formula I, can be used as the active compound in the preparation of liposomal formulations of this example.

EXAMPLE 23

Determination of Activity Utilizing Alex Cells in vitro Assay

This procedure is a modification of a procedure initially described by Chen et al., *Biochemical Pharmacology*, 36 (24), 4361–4362 (1987).

A301 (Alex) cells are pre-infected with a constant amount of HIV (LAV Strain) for three hours at 37° C. Test compounds and AZT (control) are added to the infected cells in two, three or five-fold dilutions, out four places for screening and eight places for confirmation. Unless mentioned the highest concentration is 200 $\mu$M. The test plates are incubated in CO$_2$ at 37° C. for up to twelve days (incubation time depends on virus pool titer) with a partial medium/sample change midpoint through the incubation period. Uninfected A301 cells with sample dilutions, but without virus, are used to evaluate cytotoxicity.

Reverse transcriptase levels are assayed at the end of the incubation period as follows, to determine if antiviral activity is present.

55 $\mu$L of medium from the HIV infected Alex cells is added to 10 $\mu$L of 3.2% Triton X-100. This solution is incubeted for 30 minutes at 37° C., then 25 $\mu$L of 4× assay mix is added to it. The 4× assay mix contains [$^3$H]TTP, poly(A).oligo(dT), potassium chloride, magnesium chloride, dithiothreitol, and Tris-HCl buffer, pH8.0. After incubating this solution for an additional 60 minutes, 20 $\mu$L is spotted on Whatman 3 MM paper. The paper is washed in 5% TCA, 1% sodium pyrophosphate for three times (10 minutes each), followed by one wash (10 minutes) in ethanol. The radioactivity remaining on the 3MM paper is quantitated by scintillation counter, and corresponds to reverse transcriptase level.

The compounds of the present invention show activity when tested by this method.

EXAMPLE 24

Kinetic Study of Reverse Transcriptase and DNA Polymerase Inhibition

This procedure is a modification of procedures initially described by Chen et al., *Molecular Pharmacology*, 25, 441–445 (1984), and as described by Wang et al., *Biochemistry*, 21, 1597–1608 (1982).

4'-Azidothymidine 5'-triphosphate was tested as an inhibitor against HIV reverse transcriptase, and against α and β DNA polymerase from human kB cells. Poly(A)oligo(dT)$_{12-18}$ was used as a template primer for the HIV reverse transcriptase assay, while activated DNA was used as a template primer for α and β DNA polymerases. 4'-Azidothymidine triphosphate was found to be a competitive inhibitor against thymidine triphosphate with a $K_i$ of 0.008 μM, 62.5 μM, and 150 μM for HIV reverse transcriptase, and α and β DNA polymerases, respectively.

EXAMPLE 25

Determination of Toxicity Effects Utilizing Human Hematopoietic Cells in vitro

This procedure is a modification of procedures initially described by Diainiak, et al., *British Journal of Haematology*, 69, 229-304 (1988), or as described by Sommadossi, et al., *Agents and Chemotherapy*, 31 (3), 452-454 (1987).

The effect of 4'-azidothymidine and AZT on the formation of erythroid and GM colonies from precursors in human peripheral blood and bone marrow were compared; from which the inhibition of 4'-azidothymidine and AZT against human hematopoietic cells were compared.

Preparation of Nonadherent Mononuclear Cells

In each experiment peripheral blood or bone marrow from a single donor was used. Human peripheral blood mononuclear cells (PBL) were separated from heparinized blood of drug-free donors by density-gradient centrifugation in Ficoll (Pharmacia). Whole blood diluted 1:1 with Hanks' balanced salt solution (HBSS, Gibco) was layered on the top of Ficoll and centrifuged at 400×g for 30 min. Cells were collected from the interphase and after washing, the concentration was adjusted to $2 \times 10^6$ cells/mL in RPMI-1640 medium with 25 mM Hepes buffer (Gibco). Monocytes were removed by adherence to plastic in large Petri dishes (150×15 mm), adding 20 ml of the cell suspension/dish, and incubating for 1 hour at 37° C. Nonadherent mononuclear cells (MN) were removed by vigorous washing of the Petri dish with warm (37° C.) HBSS.

Preparation of Bone Marrow Mononuclear Cells (BM)

Bone marrow aspirates from healthy donors were collected in heparizined syringes. The whole mononuclear cell fraction was separated by Ficoll-Paque density-gradient centrifugation (400×g for 30 min). Cells collected from the interphase were washed 3 times in HBSS and resuspended in culture medium as described below for CFU-GM assay.

CFF-GM Assay (Myeloid Precursors)

MN ($1.5 \times 10^6$ cells/ml) and BM ($1. \times 10^5$ cells/ml) were cultured in complete medium as follows: Dulbecco's Modified Eagle Medium (DMEM, Gibco) supplemented with 20% heat-inactivated fetal calf serum (FCS, Hyclone), 2 mM L-glutamine, $5 \times 10^{-5}$M 2-mercaptoethanol, penicillin (100 U/ml), streptomycin (100 μg/ml), and 0.3% bacto-agar (Difco). All supplements were from Gibco, unless otherwise specified. Cells were plated in 35×100 mm Lux Petri dishes (suspension dishes) in triplicate, and incubated at 37° C. with 5% $CO_2$ in air at 100% humidity. A supernatant from a T-cell line (GCT, Gibco), containing GM-Colony Stimulating Factor (GM-CSF), was used at a final concentration of 10% in complete medium. Tested compounds were added to the test dishes at concentrations of $10^{-9}$ to $10^{-4}$M. Cells were incubated in air containing 5% $CO_2$ (100% humidity) at 37° C. for 14 days. Colonies were counted under a dissecting microscope. A CFU-GM colony was defined as a cluster of 50 or more cells consisting of granulocytes, monocyte-macrophages, or both.

BRU-E Assay (for easly Erythroid Precursors) and CFU-E Assay (for Late Erythroid Precursors)

MN were cultured at a concentration of $3 \times 10^5$ cells/ml. The culture medium consisted of Iscove's Modified Eagle Medium (Gibco) supplemented with 30% heat-inactiviated FCS (Hyclone), penicillin (100 ml), streptomycin (100 μg/ml), 2-mercaptoethanol ($1 \times 10^{-4}$, 1% deionized bovine serum albumin (BSA, Sigma), DEAE-Dextran 40 μg/ml (Pharmacia), 0.8% methylcellulose (4000 Centipose, Fisher), and erythropoietin 2 U/ml (Connaught Laboratories). Cells were plated in 96-well plates (200 μl/well) and incubated at 37° C. with 5% $CO_2$ in air (100% humidity) for 7-14 days. CFU-E colonies were counted on Days 7-8. Clusters of 8 or more hemoglobinized cells were considered as a colony. BFU-E colonies were counted on Day 14. Aggregates of 50 or more cells were counted as a colony. Colonies were confirmed as erythroid by benzidine stainings.

Statistical Analysis

All tests were performed in triplicate. The 50% inhibitory concentrations ($IC_{50}$) for all types of colonies were determined using an RS 1 program on an IBM-PC.

Compounds of the present invention show decreased toxicity when compared with AZT by this method.

EXAMPLE 26

Determination of Activity Utilizing Friend Leukemia Virus in Mice

This procedure is a modification of a procedure initially described by Jones et al., *Journal of Virology*, 62 (2), 511-518 (1988), or by modifications thereof.

Friend leukemia virus complex (FLVC) was used. This retrovirus complex consists of both helper and defective virus particles.

Six week old female Balb/c mice from Bantin and Kingman, each weighing on the average of 18 gm, received 0.2 ml of a solution (comprised of virus diluted in PBS containing 0.002M EDTA) administered at 20 FFU/mouse, intravenously. Treatments began 4 hours after infection and continued for 9 days. AZT and 4'-azidothymidine were administered at 60 mg/kg/dose twice daily on Days 0, 4, and 5; and on Days 1-3 and 6-8 were administered 3 times daily at 40 mg/kg/dose. 2'3'-Dideoxycytidine was administered at 120 mg/kg/dose twice daily on days 0, 4, and 5; and on days 1-3 and 6-8 was administered 3 times daily at 80 mg/kg/dose. All treatments were given intraperitoneally, 0.5 ml/dose. On day 9 after infection the spleens were removed, stained and fixed in Bouin's solution for 2 hours and then weighed. Foci were counted on spleens. A standard t-test was run to compare difference in spleen weights and difference in number of foci-forming units (FFU's) per spleen between groups.

Compounds of the present invention show anti-viral activity when tested by this method.

EXAMPLE 27

4'-Azido-5-chloro-2'-deoxyuridine

To 4'-azido-3',5'-di-0-acetyl-2'-deoxyuridine (176 mg, 0.5 mM), prepared, for example, as described in Preparation 9, in a solution of 10 mL of anhydrous pyridine is added N-chlorosuccinimide (100 mg, 0.75 mM). The mixture is heated to 100° C. for 30 min, cooled to room temperature and the solvent is evaporated. To the resulting residue is added a solution of ammonia in methanol (5 mL) and the mixture is stirred at room temperature for 6 hours. Evaporation of the solvent, chromatography and crystallization from ethanol gives the title compound, 4'-Azido-5-chloro-2'-deoxyuridine.

EXAMPLE 28

4'-Azido-5-bromo-2'-deoxyuridine

4'-azido-3',5'-di-0-acetyl-2'-deoxyuridine (333 mg, 1.0 mM), prepared, for example, as described in Preparation 9, in a solution of 20 mL of glacial acetic acid is added N-bromosuccinimide (270 mg, 1.5 mM). The resulting mixture is heated to reflux for a period of 30 min, cooled to room temperature and the solvent evaporated under reduced pressure. The resulting residue is treated with a concentrated solution of ammonia in methanol (10 mL) and the mixture is stirred at room temperature for 5 hours. Evaporation of the solvent, chromatography and crystallization gives the title compound, 4'-Azido-5-bromo-2'-deoxyuridine.

EXAMPLE 29

4'-Azido-2'-deoxy-5-iodouridine

To 4'-azido-3',5'-di-0-acetyl-2'-deoxyuridine (176 mg, 0.5 mM), prepared, for example, as described in Preparation 9, in methanol (10 mL) is added a solution of iodine monochloride in methanol (0.15M). The mixture is heated at reflux for 3 hours, cooled to room temperature and the solvent is evaporated under reduced pressure. A saturated solution of ammonia in methanol (5 mL) is added to the residue and the mixture is stirred at room temperature for 4 hours. Evaporation of the solvent followed by chromatography on silica gel and crystallization from methanol gives the title compound, 4'-Azido-2'-deoxy-5-iodouridine.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula

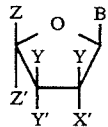

wherein:

B is a purine or a pyrimidine;

X and X' are H, OH or F, provided that at least one is H;

Y and Y' are H, OH, OCH$_3$ or F, provided that at least one is H;

Y' and Z together form a cyclic phosphate ester, provided that Y is H; or

Z is

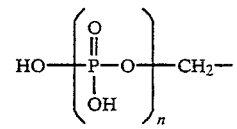

where n is zero, one, two or three; and Z' is N$_3$ or OCH$_3$;

provided that when X' and Y' are OH and Z' is N$_3$, B is not cytosine, and when X' and Y' are OH and Z' is OCH$_3$, B is not uracil, adenine or cytosine; or a pharmaceutically acceptable ester, ether or salt thereof.

2. The compound of claim 1, where B is selected from the group consisting of: adenine, guanine, hypoxanthine, uracil, thymine, cytosine, 2,6-diaminopurine, 2-aminopurine, 8-aminopurine, 5-ethyl-2,4-dioxopyrimidine, 5-propyl-2,4-dioxopyrimidine, 5-(2-bromo-1-ethenyl)-2,4-dioxopyrimidine, 5-halo-2,4-dioxopyrimidine, and 5-trifluoromethyl-2,4-dioxopyrimidine.

3. The compound of claim 2, where Z' is N$_3$.

4. The compound of claim 2, where Z' is OCH$_3$.

5. The compound of claim 2, where n is zero.

6. The compound of claim 2, where B is thymine.

7. The compound of claim 2, where B is cytosine.

8. The compound of claim 2, where B is uracil.

9. The compound of claim 2, where B is guanine.

10. The compound of claim 2, where B is adenine.

11. The compound of claim 2, where B is 5-halo-2,4-dioxopyrimidine.

12. The compound of claim 6 that is 4'-azidothymidine.

13. The compound of claim 6 that is 3'-fluoro-4'-methoxythymidine.

14. The compound of claim 11 that is 1-(4-azido-2-deoxy-β-D-erthyro-pentofuranosyl)-5-chloro-2,4-dioxopyrimidine.

15. The compound of claim 11 that is 1-(4-azido-2-deoxy-β-D-erthyro-pentofuranosyl)-5-bromo-2,4-dioxopyrimidine.

16. A compound of the formula

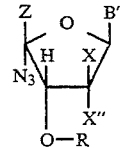

wherein:

B' is a purine or a pyrimidine, or an acylated equivalent thereof;

R is methyl or an acyl group;

X is H or F;

X" is H, F, or the group —O—R, provided that at least one of X or X" is H; and

Z is iodomethyl or bromomethyl, provided that when Z' is iodomethyl and X" is —O—R and R is benzoyl, B' is not N$^4$-benzoylcytosine.

17. The compound of claim 16 where Z is iodomethyl.

18. The compound of claim 16 where R is anisoyl, benzoyl, acetyl or furan-2-carbonyl.

19. The compound of claim 16, where R is anisoyl.

20. The compound of claim 16, where R is benzoyl.

21. A pharmaceutical composition comprising a pharmaceutically acceptable non-toxic excipient and therapeutically effective amount of a compound of the formula

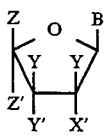

wherein:

B is a purine or a pyrimidine;

X and X' are H, OH or F, provided that at least one is H;

Y and Y' are H, OH, OCH$_3$ or F, provided that at least one is H;

Y' and Z together form a cyclic phosphate ester, provided that Y is H; or

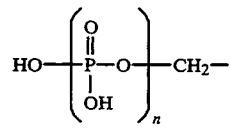

where n is zero, one, two or three; and

Z' is N$_3$ or OCH$_3$; provided that when X' and Y' are OH and Z' is N$_3$, B is not cytosine, and provided that when X' and Y' are OH and Z' is OCH$_3$, B is not uracil, or cytosine;

or a pharmaceutically acceptable ester, ether or salt thereof.

* * * * *